(12) United States Patent
Booth et al.

(10) Patent No.: US 12,688,921 B2
(45) Date of Patent: Jul. 21, 2026

(54) ADVISING DIABETES TREATMENTS

(71) Applicant: GLYTEC, LLC, Waltham, MA (US)

(72) Inventors: Robert C. Booth, Greer, SC (US);
John G. Clark, Atlanta, GA (US)

(73) Assignee: GLYTEC, LLC, Boston, MA (US)

( * ) Notice: Subject to any disclaimer, the term of this patent is extended or adjusted under 35 U.S.C. 154(b) by 0 days.

(21) Appl. No.: 18/670,992

(22) Filed: May 22, 2024

(65) Prior Publication Data

US 2024/0321423 A1     Sep. 26, 2024

Related U.S. Application Data

(63) Continuation of application No. 18/182,249, filed on Mar. 10, 2023, now Pat. No. 12,002,563.

(60) Provisional application No. 63/269,181, filed on Mar. 11, 2022.

(51) Int. Cl.
G16H 20/17          (2018.01)
G16H 50/30          (2018.01)
(52) U.S. Cl.
CPC .............. G16H 20/17 (2018.01); G16H 50/30 (2018.01)
(58) Field of Classification Search
CPC ........ G16H 10/60; G16H 10/20; G16H 20/00; G16H 50/30; G16H 20/30
See application file for complete search history.

(56) References Cited

U.S. PATENT DOCUMENTS

| | | | | |
|---|---|---|---|---|
| 9,351,670 | B2 * | 5/2016 | Dunn | G16H 40/67 |
| 10,380,328 | B2 | 8/2019 | Booth et al. | |
| 11,200,988 | B2 * | 12/2021 | Booth | G16H 50/00 |
| 12,027,274 | B2 * | 7/2024 | Kahlbaugh | G16H 50/50 |
| 2014/0088392 | A1 | 3/2014 | Bernstein et al. | |
| 2017/0220751 | A1 | 8/2017 | Davis et al. | |
| 2019/0252079 | A1 | 8/2019 | Constantin et al. | |
| 2020/0152335 | A1 * | 5/2020 | Prodhom | G16H 50/50 |
| 2020/0402636 | A1 | 12/2020 | Booth et al. | |

OTHER PUBLICATIONS

International Search Report and Written Opinion for the related Application No. PCT/US2023/064200, dated Jun. 6, 2023, 56 pages.

* cited by examiner

*Primary Examiner* — Eliza A Lam
(74) *Attorney, Agent, or Firm* — Honigman LLP; Brett A. Krueger; Grant Griffith

(57)          ABSTRACT

A method for managing glucose levels of a patient under the supervision of a healthcare professional (HCP). The method includes obtaining patient information for the patient, the patient information comprising patient medication data, patient monitoring data, and patient characteristic data. The method also includes creating a patient risk profile based on the patient information. The method also includes determining a likelihood that the patient will experience hyperglycemic effects based on the patient risk profile. The method also includes determining an optimum treatment plan for the patient based on the patient risk profile and the likelihood that the patient will experience hyperglycemic effects. The method also includes executing the optimum treatment plan.

20 Claims, 20 Drawing Sheets

360, 360a

Medications

| MedicationID | ClassID | MedGenericName | MedBrandName | RouteID | DosageFormID | HyperSS | HyperLS | HypoSS | HypoLS | MinEfficacyTime | HalfLife |
|---|---|---|---|---|---|---|---|---|---|---|---|
| 1 | 4 | methylprednisolone | Solu-Medrol (Pro) | 1 | 5 | 5 | 3 | 0 | 0 | 60 | 720 |
| 2 | 4 | methylprednisolone | Duralone | 1 | 5 | 5 | 3 | 0 | 0 | 60 | 720 |
| 3 | 6 | atenolol | Tenormin | 1 | 7 | 0 | 0 | 4 | 1 | 180 | 450 |

364, 364a

RiskProfileCharacteristics

| ID | BiomarkerID | ValueMin | ValueMax | RiskProfileID |
|---|---|---|---|---|
| 1 | 1 | 65 |  | 1 |
| 2 | 2 | 8 |  | 1 |
| 3 | 3 | 30 |  | 1 |

362, 362a

RiskProfiles

| RiskProfileID | HyperSS | HyperLS | HypoSS | HypoLS | MedicationID |
|---|---|---|---|---|---|
| 1 | 5 | 3 | 0 | 0 | 1 |

366, 366a

Biomarkers

| BiomarkerID | Name | UnitofMeasure |
|---|---|---|
| 1 | Age | years |
| 2 | HbA1C | % |
| 3 | BMI | kg/m2 |

FIG. 2C

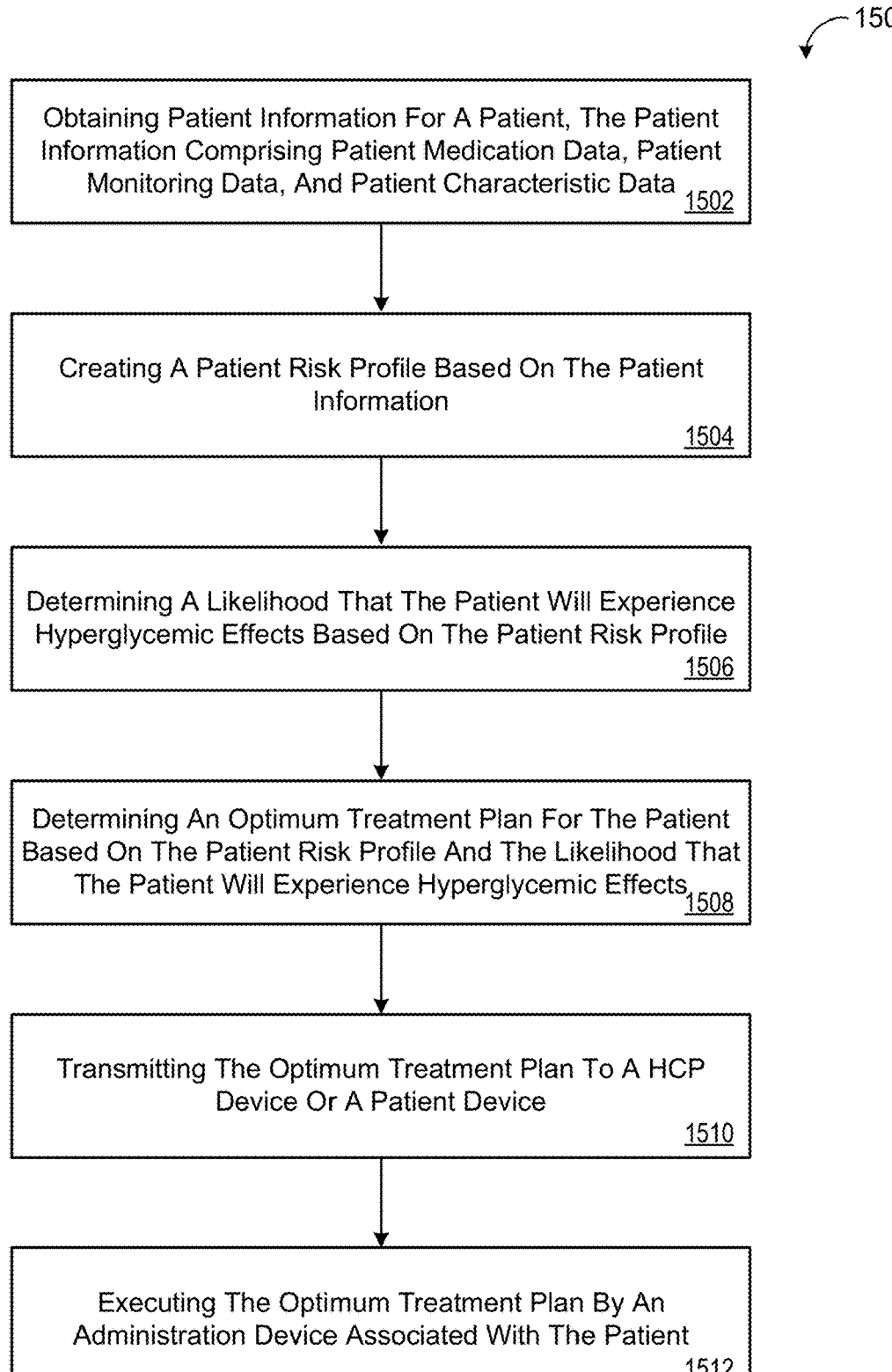

1500

Obtaining Patient Information For A Patient, The Patient Information Comprising Patient Medication Data, Patient Monitoring Data, And Patient Characteristic Data _1502_

Creating A Patient Risk Profile Based On The Patient Information _1504_

Determining A Likelihood That The Patient Will Experience Hyperglycemic Effects Based On The Patient Risk Profile _1506_

Determining An Optimum Treatment Plan For The Patient Based On The Patient Risk Profile And The Likelihood That The Patient Will Experience Hyperglycemic Effects _1508_

Transmitting The Optimum Treatment Plan To A HCP Device Or A Patient Device _1510_

Executing The Optimum Treatment Plan By An Administration Device Associated With The Patient _1512_

FIG. 14

ADVISING DIABETES TREATMENTS

CROSS REFERENCE TO RELATED APPLICATIONS

This U.S. patent application is a continuation of, and claims priority under 35 U.S.C. § 120 from, U.S. patent application Ser. No. 18/182,249, filed on Mar. 10, 2023, which claims priority under 35 U.S.C. § 119(e) to U.S. Provisional Application No. 63/269,181, filed on Mar. 11, 2022. The disclosures of these prior applications are considered part of the disclosure of this application and are hereby incorporated by reference in their entireties.

TECHNICAL FIELD

This disclosure relates to recommending therapy regimens for treating various types and classification levels of Diabetes Mellitus.

BACKGROUND

According to recent data from the American Diabetes Association and Centers for Disease Control and Prevention (CDC), there are more than 34 million adults in the United States living with diabetes. The International Diabetes Federation reports the global incidence of diabetes at 463 million adults and estimates that number will rise to 700 million by 2045.

In the acute care setting, all patients, both with and without diabetes, are vulnerable to safety risks surrounding glycemic control. Any hospitalized patient, at any time, may experience hyperglycemia—a state of elevated blood glucose brought on by the stress of illness or treatment received. For this reason, approximately 30-40% of inpatients require insulin therapy during their stay, a medication that—although widely prescribed and necessary—is inherently dangerous. Insulin is involved in 16.3% of medication error reports for high-alert medications, more than any other mediation type. Insulin is considered a high-alert medication because it has the potential to cause significant patient harm if misused.

Improper insulin management, including the overtreatment, undertreatment or mistreatment of hyperglycemia, can lead to hypoglycemia (a state of abnormally low blood glucose), and potentially catastrophic consequences, such as coma, kidney failure, stroke, paralysis, sepsis, brain damage, cardiac arrest and/or death.

Optimal glucose management in the hospital setting can improve patient outcomes and reduce the risk of complications and death. Poor glucose management in the hospital is commonplace and can increase a patient's risk for infection, recurrent admission to the hospital and extend a patient's hospital length of stay. One episode of severe hypoglycemia, most often caused by too large of an insulin dose, can have a significant impact on a patient's health and financial well-being.

Clinicians often lack the specialized diabetes expertise needed to effectively identify hyperglycemia and determine an optimal therapy pathway. Patients with hyperglycemia often may receive a wide array of medications including non-insulin oral antihyperglycemic medications, long-acting insulin, rapid-acting insulin, and non-insulin injectable anti-hyperglycemic medications. Moreover, there are several medications and therapy options available for providers to choose depending on a patient's individual needs. There exists a need for a system to guide clinicians as to the most appropriate therapy, medication, and protocol for management of optimal glycemia in the hospital.

SUMMARY

One aspect of the disclosure provides a computer-implemented method for managing glucose levels of a patient under the supervision of a healthcare professional (HCP). The method when executed by data processing hardware causes the data processing hardware to perform operations including obtaining patient information for the patient, the patient information comprising patient medication data, patient monitoring data, and patient characteristic data. The method includes creating a patient risk profile based on the patient information. The method includes determining a likelihood that the patient will experience hyperglycemic effects based on the patient risk profile. The method includes determining an optimum treatment plan for the patient based on the patient risk profile and the likelihood that the patient will experience hyperglycemic effects. The method includes transmitting the optimum treatment plan to one of a HCP device associated with the HCP or a patient device associated with the patient.

Implementations of the disclosure may include one or more of the following optional features. In some implementations, the type of diabetes associated with the patient comprises Type 1 diabetes mellitus, Type 2 diabetes mellitus, gestational diabetes mellitus, non-diabetic stress hyperglycemia, Maturity Onset Diabetes of the Young (MODY), Latent Autoimmune Diabetes in Adults (LADA), or unknown.

The patient medication data may comprise a current medications list including a list of medications and corresponding dosages the patient is currently prescribed. The patient medication data may comprise drug name, dosage, route of administration, frequency, and datetime of administration of any medications known to impact patient blood glucose levels that the patient is currently prescribed. The method may further include determining, by the data processing hardware, whether the medications in the current medications list are likely to cause the patient to experience hyperglycemic effects.

The patient information may further comprise at least one of current medical conditions associated with the patient, permanent medical conditions associated with the patient, one or more glucose values for the patient, or an A1c value for the patient.

The patient characteristic data may comprise at least one of nutrition order data associated with the patient, a medical administration record (MAR) associated with the patient, an electronic medical record (EMR) associated with the patient, or laboratory information system (LIS) data associated with the patient.

The patient medication data may comprise drug name, dosage, route of administration, frequency, and datetime of administration of any medications known to impact patient blood glucose levels that the patient is currently prescribed.

The patient risk profile may be created further based on medical literature.

The patient risk profile may be created by matching the patient information to a previously-created patient risk profile for a patient with similar patient information.

Another aspect of the disclosure provides a computer-implemented method for managing glucose levels of a patient under the supervision of a healthcare professional (HCP). The method when executed by data processing hardware causes the data processing hardware to perform operations including obtaining patient information for the patient, the patient information comprising patient medication data, patient monitoring data, and patient characteristic data. The method includes creating a patient risk profile based on the patient information. The method includes determining a likelihood that the patient will experience hyperglycemic effects based on the patient risk profile. The method includes determining an optimum treatment plan for the patient based on the patient risk profile and the likelihood that the patient will experience hyperglycemic effects. The method includes executing, by an administration device associated with the patient, the optimum treatment plan. This aspect may include one or more of the following option features.

In some implementations, the administration device comprises at least one of an insulin pump, a smart pen, a smart pill bottle, a smart pill, or an insulin inhaler.

The patient medication data may comprise a current medications list including a list of medications and corresponding dosages the patient is currently prescribed, and a drug name, dosage, route of administration, frequency, and datetime of administration of any medications known to impact patient blood glucose levels that the patient is currently prescribed. The method may further comprise determining, by the data processing hardware, whether the medications in the current medications list are likely to cause the patient to experience hyperglycemic effects.

The patient information may further comprise at least one of current medical conditions associated with the patient, permanent medical conditions associated with the patient, one or more glucose values for the patient, or an A1c value for the patient.

The patient characteristic data may comprise at least one of nutrition order data associated with the patient, a medical administration record (MAR) associated with the patient, an electronic medical record (EMR) associated with the patient, or laboratory information system (LIS) data associated with the patient.

The patient medication data may comprise drug name, dosage, route of administration, frequency, and datetime of administration of any medications known to impact patient blood glucose levels that the patient is currently prescribed.

The patient risk profile may be created further based on medical literature.

The patient risk profile may be created by matching the patient information to a previously-created patient risk profile for a patient with similar patient information.

The details of one or more implementations of the disclosure are set forth in the accompanying drawings and the description below. Other aspects, features, and advantages will be apparent from the description and drawings, and from the claims.

DESCRIPTION OF DRAWINGS

FIGS. 2B and 2C are schematic views of exemplary components of the program of FIG. 2A.

FIG. 14 is a flowchart of an example arrangement of operations for a method of managing glucose levels in a patient under the supervision of a healthcare professional. Like reference symbols in the various drawings indicate like elements.

DETAILED DESCRIPTION

Diabetes is one of the most prevalent and expensive medical conditions requiring prescription therapy, estimated to affect more than 34 million people in the United States. In the acute care setting, all patients, both with and without diabetes, are vulnerable to safety risks surrounding glycemic control. Glycemic control may be affected by other non-insulin medications that the patient is taking and clinical biomarkers associated with the patient, with glucose inputs associated with the patient helping to guide the treatment of patients with diabetes. With the many decisions that a healthcare provider must make for treating a patient's diabetes, it is desirable to have a clinical support system 100 (FIGS. 1A and 1B) that advises and manages a glycemic formulary, glycemic telemetry, therapy selection, therapy adjustment, and/or therapy change.

Clinicians may maintain the glucose levels of diabetic inpatients affected by diabetes by using various combinations of therapies that includes dosages of insulin, dietary and exercise management, and anti-diabetes medications (ADMs). However, a wide variety of therapies are available for treating diabetes, each of which may be associated with various characteristics. Therefore, it is desirable to have a clinical support system 100 (FIGS. 1A and 1B) that advises and manages selection of tailored therapies for patients that are both precise and effective. Moreover, the clinical support system will make treatment recommendations to healthcare professionals as to: a risk assessment that the patient will experience hyperglycemic or hypoglycemic effects; how and when the healthcare professional should monitor the patient via inpatient glycemic telemetry; optimal times to initiate, intensify, modify, adjust, or discontinue insulin therapy; and optimal times to transition from insulin to non-insulin therapies or vice versa. As will become apparent, the clinical support system 100 provides a unified platform for managing and advising treatment of patients of all types and classifications of diabetes.

Figure 1A:
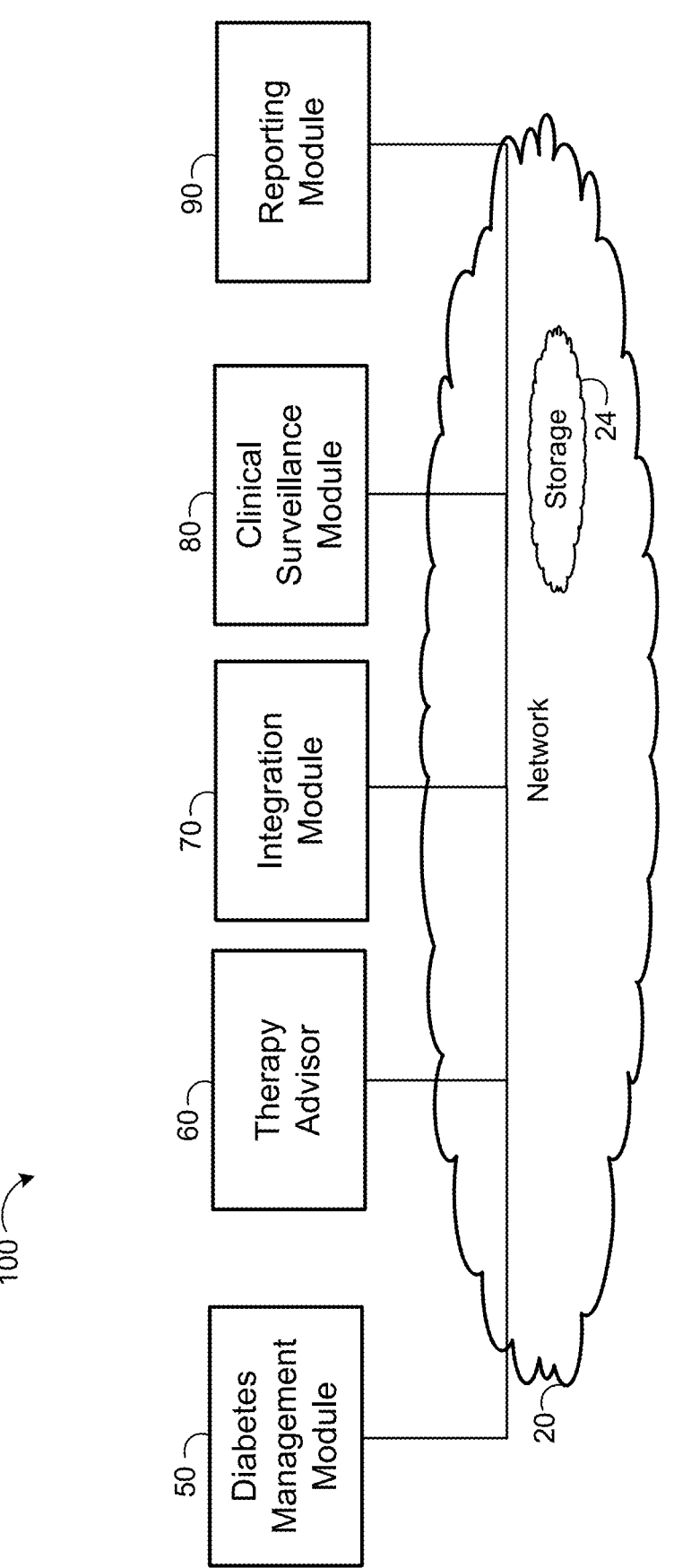
FIG. 1A is a schematic view of an exemplary system for managing glucose levels of a patient.
Figure 1B:
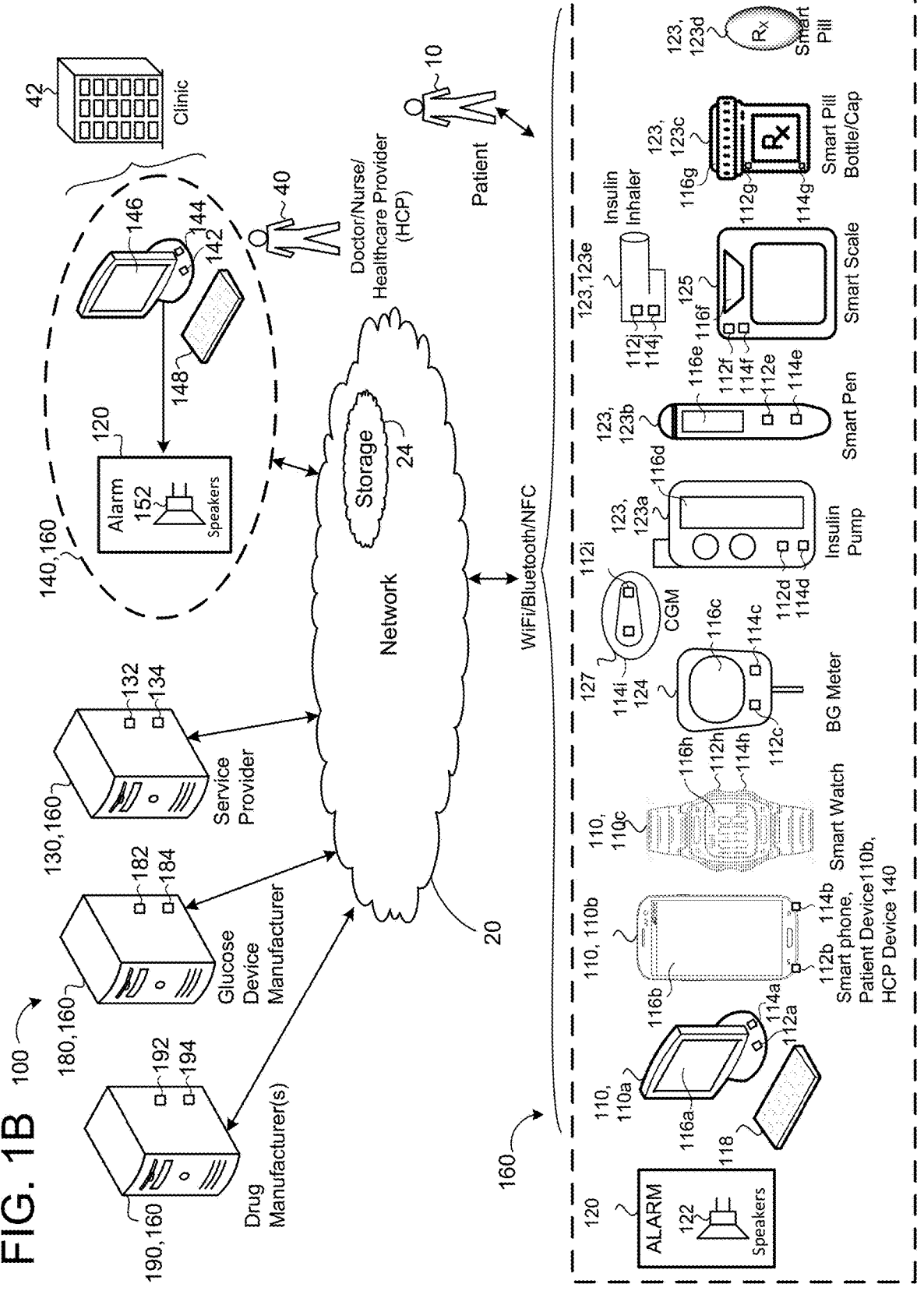
FIG. 1B is a schematic view of an exemplary system for managing glucose levels of a patient.

Referring to FIGS. 1A and 1B, in some implementations, a clinical support system 100 analyzes inputted patient condition parameters for a patient 10 and selects and manages a personalized treatment regimen to adjust and maintain a glucose level or target A1C of the patient 10 within a target range. As used herein, the patient 10 may refer to an outpatient that may be located at some remote location, such as the patient's 10 residence or place of employment, or an inpatient that may be located at a medical facility, such as a hospital. As used herein, the term "clinic" or "clinical" may refer to a location in which care managers provide healthcare services to patients. The system 100 includes a first program implemented in connection with one or more of: a personal computer 110, 110a of a patient 10; a patient device 110, 110b (e.g., mobile phone, tablet); a smart wearable 110, 110c (e.g., smart watch, fitness tracker); an administration device 123, including an insulin pump 123, 123a, a smart pen 123, 123b, a smart pill bottle 123, 123c, a smart pill 123, 123d configured to detect and communicate ingestion, an insulin inhaler 123, 123e; a glucose meter (commonly referred to as "glucometer") 124; a continuous glucose monitor (CGM) 127; a body weight scale 125, a service provider or health care professional (HCP) device 140; and/or a service provider 130. The glucose meter 124 and CGM 127 may be collectively referred to as a glucose measurement device 124, 127. While the glucose meter 124 and CGM 127 are described as exemplary glucose measurement devices for obtaining glucose measurements, any device/mechanism/equipment capable of measuring glucose, or otherwise obtaining glucose levels, may be used by the system 100. For instance, optical and/or electrochemical techniques may be used to measure glucose levels from fluids such as, but not limited to, blood, interstitial fluid, saliva, and sweat.

The system 100 further includes a second program, or dosing controller 160, that may reside in one or more of the patient device 110, the HCP device 140, and/or the service provider 130. The dosing controller 160 provides advice on the selection of a therapy recommendation and dosing of medications associated with the selected therapy recommendation along with a risk assessment that the patient will experience a hyperglycemic or hypoglycemic event. As used herein, the medications associated with a selected therapy recommendation can include insulin and/or combinations of one or more non-insulin medications (e.g., ADMs) to manage the patient's 10 glucose values. Therapy recommendations can additionally include dietary and exercise instructions in addition to, or in lieu of, and/or non-insulin medications. Selection and dosing advice can be determined by obtaining a health status of the patient 10. The health status incudes: real-time data transmitted by the patient device(s) 110, 123, 124, 125, 127, 129; digital downloads from the patient device(s) 110, 123, 124, 125, 127, 129; laboratory tests; and judgement-based assessments by the HCP 40 and the patient 10. As will become apparent, the health status of the patient 10 along with other patient characteristics are used in a glycemic formulary to determine a risk assessment that the patient will experience hyperglycemic or hypoglycemic effects.

The use of the health status in the glycemic formulary is accomplished by the dosing controller 160, which then provides an output corresponding a therapy recommendation, a telemetry recommendation, and/or a therapy modification. The results are used to improve glycemic control of the patient 10 by adjusting the selection and dosing of insulin and/or non-insulin medications. Selection and dosing may be controlled automatically by the dosing controller 160, or may include communicating information to the HCP 40 in real-time so that the HCP 40 can manually adjust the treatment for the patient 10. In other implementations, selection and dosing may include communicating information to the patient 10 in real-time so that he/she can manually adjust his/her dosages.

Referring to FIGS. 1A and 1B, the clinical support system 100 includes a glycemic management module 50, a therapy advisor module 60, an integration module 70, a surveillance module 80, and a reporting module 90. Each module 50, 60, 70, 80, 90 is in communication with the other modules 50, 60, 70, 80, 90 via a network 20. In some examples, the network 20 (discussed below) provides access to cloud computing resources that allows for the performance of services on remote devices instead of the specific modules 50, 60, 70, 80, 90. The glycemic management module 50 executes the program 160 (e.g., an executable instruction set) on a computing device 112, 132, 142 or on the cloud computing resources. The therapy advisor module 60 provides the HCP 40 with a plurality of information and recommendations to enable the HCP 40 to provide an improved therapy to the patient 10. The integration module 70 allows for the interaction of users 40 and patients 10 with the system 100. The integration module 70 receives information inputted by a user 40 and allows the user 40 to retrieve previously inputted information stored on a storage system (e.g., one or more of cloud storage resources 24, a non-transitory memory 144 of an electronic medical system 140 of a clinic 42 or telemedicine facility, a non-transitory memory 114 of the patient device 110, a non-transitory memory 134 of the service provider's system 130, or other non-transitory storage media in communication with the integration module 70). The storage resources 24 and non-transitory memory 114, 134, 144 may individually or collectively be referred to as memory hardware. Therefore, the integration module 70 allows for the interaction between the HCPs 40, patients 10, and the system 100 via a display 116, 146. The surveillance module 80 considers patient information received from a HCP 40 via the integration module 70 and information received from a glucometer 124 or CGM 127 that measures a patient's glucose value and determines if the patient 10 is within a threshold glucose value. Generally, the glucometer 124 measures capillary "blood glucose" values and the CGM 127 measures "interstitial glucose" values that can be correlated to blood glucose values. As used herein, the term "glucose value" refers to either one of blood glucose, interstitial glucose, or any other technique that can be used to correlate blood glucose values from measured glucose values in body fluids. Moreover, use of the term "blood glucose" is not meant to imply that the CGM 127 was not used due to the correlation between interstitial glucose and blood glucose. In some examples, the surveillance module 80 alerts the user 40 if a patient's glucose values are not within a threshold glucose value. The surveillance module 80 may be preconfigured to alert the user 40 of other discrepancies between expected values and actual values based on preconfigured parameters. For example, when a patient's glucose value drops below a lower limit of the threshold glucose value. The reporting module 90 may be in communication with at least one display 116, 146 and provides information to the user 40 determined using the glycemic management module 50, the integration module 70, and/or the surveillance module 80. In some examples, the reporting module 90 provides a report that may be displayed on a display 116, 146 and/or is capable of being printed.

The system 100 is configured to evaluate a glucose level, a nutritional intake, other non-insulin medications taken, and a lifestyle of a patient 10. Based on the evaluation and analysis of the data, the system 100 selects and executes a treatment/therapy regimen, which is administered to the patient 10 to adjust and maintain the glucose value of the patient 10 into a glucose target range. The system 100 may be applied to various devices, including, but not limited to, patient devices 110, subcutaneous insulin infusion pumps 123a, smart pens 123b, smart pill bottles 123c, smart pills 123d, insulin inhalers 123e, glucometers 124, CGM 127, and smart scales 125. Insulin infusion pumps 123a may include infusion pumps for injecting fast-acting or rapid-acting insulins subcutaneously or patch-based pumps configured to deliver one of multiple fixed and flat basal rates for a day and fixed units to cover meals. Smart pens 123b may include insulin pens for injecting insulin to the patient 10 subcutaneously as well as non-insulin pens for injecting non-insulin medications (e.g., ADMs) to the patient subcutaneously. The insulin inhaler 123d may be used for inhaling a rapid-acting insulin as a surrogate for subcutaneously administering a short- or rapid-acting bolus insulin.

In some examples, the clinical support system 100 includes the network 20, the patient device 110, the dosing controller 160, a service provider 130, and a glucose device manufacturer provider 180. The patient device 110 may include, but is not limited to, desktop computers 110a or portable electronic device 110b (e.g., cellular phone, smartphone, personal digital assistant, barcode reader, personal computer, or a wireless pad), activity trackers 110c (e.g., smart watch, fitness band) or any other electronic device capable of sending and receiving information via the network 20. In some implementations, one or more of the patient's glucometer 124, CGM 127, insulin pump 123a, pen 123b, bottle/cap 123c, or insulin inhaler 123d are capable of sending and receiving information via the network 20.

The patient device 110a, 110b, 110c includes a data processor 112a, 112b, 112h (e.g., a computing device that executes instructions), non-transitory memory 114a, 114b, 114h and a display 116a, 116b, 116h (e.g., touch display or non-touch display) in communication with the data processor 112a, 112b, 112h. In some examples, the patient device 110 includes a keyboard 118, speakers 122, microphones, mouse, and a camera.

The insulin pump 123a, pen 123b, inhaler 123e, glucometer 124, and CGM 127 associated with the patient 10 may include a data processor 112c, 112d, 112e, 112i, 112j (e.g., a computing device that executes instructions), and non-transitory memory 114c, 114d, 114e, 114i, 114j and/or a display 116c, 116d, 116e (e.g., touch display or non-touch display) in communication with the data processor 112c, 112d, 112e, 112i, 112j. The devices 123a, 123b, 123e, 124, 127 may also communicate wirelessly through the network 20 and/or with any other patient device 110, 123a, 123b, 123e, 124, 125, 127 through the same or different network 20.

The smart scale 125 and the smart bottle 123c each include a data processor 112f, 112g, (e.g., a computing device that executes instructions). The smart scale 125 and the smart bottle 123c further include non-transitory memory

114f, 114g and a display 116f, 116g (e.g., touch display or non-touch display) in communication with the data processor 112f, 112g.

The clinical support system 100 may also include a glucose device manufacturer provider 180 including a data processor 182 in communication with non-transitory memory 184. The data processor 182 may execute a proprietary download program for downloading glucose data from the memory 114c of the patient's glucometer 124 and/or from the memory 114i of the patient's CGM 127 (or other user device 110 paired to the glucometer 124 and/or CGM 127 for reading and storing measurements obtained from the corresponding glucose device 124, 127). In some implementations, the health care provider system 140 implements the proprietary download program on a computing device 142 or the proprietary download program is implemented on the patient device 110 for downloading the glucose data from the memory 114c, 114i. In some examples, the download program exports a glucose data file for storage in the non-transitory memory 24, 114, 144. The data processor 182 may execute a web-based application for receiving and formatting glucose data transmitted from one or more patient devices 110a, 110b, 124, 123a, 123b, 123c, 123e, 127 and storing the glucose data in non-transitory memory 24, 114, 144.

The drug manufacturer provider 190 may include a data processor 192 in communication with non-transitory memory 194. The memory 194 may store prescribing drug information and published guidelines, and the data processor 192 may provide the prescribing drug information and the published guidelines to the dosing controller 160 for outputting a corresponding selection and dosing of a treatment regimen for the patient 10 based on the health status of the patient 10.

The services provider 130 may include a data processor 132 in communication with non-transitory memory 134. The service provider 130 provides the patient 10 and HCP 40 with a therapy regimen program 200 (see FIG. 1D) (e.g., a mobile application, a web-site application, or a downloadable program that includes a set of instructions) executable on a computing device 112, 132, 142 of the dosing controller 160 and accessible through the network 20 via the patient device 110, health care provider electronic medical record systems 140, portable glucose measurement devices 124, 127 (e.g., glucose meter, glucometer, or CGM), or portable administration devices 123a, 123b, 123c, 123e.

In some implementations, the HCP medical record system 140 is located at a doctor's office, clinic 42, or a facility administered by a hospital (such as a hospital call center) and includes a data processor 142, a non-transitory memory 144, and a display 146 (e.g., touch display or non-touch display). The non-transitory memory 144 and the display 146 are in communication with the data processor 142. In some examples, the HCP electronic medical system 140 includes a keyboard 148 in communication with the data processor 142 to allow a user 40 to input data. The HCP electronic medical system 140 may also be in communication with an alarm 120 that is configured to emit sound via speakers 152 to alert the HCP 40 of an urgent item. The non-transitory memory 144 maintains patient records capable of being retrieved, viewed, and, in some examples, modified and updated by authorized hospital personal on the display 146. In some implementations, the HCP device 140 includes a smart phone, smartwatch, tablet computer, laptop computer, or any other suitable computing device.

The dosing controller 160 is in communication with the glucose measurement devices 124, 127 and the administration devices 123, and includes a computing device 112, 132, 142 and non-transitory memory 114, 134, 144 in communication with the computing device 112, 132, 142. The dosing controller 160 executes the therapy regimen program 200. The therapy regimen program 200 stores patient related information retrieved from the glucose measurement devices 124, 127, patient devices 110, and/or smart scale 125 and generates a therapy recommendation, that includes a selection of one or more medications associated with the therapy recommendation as well as dosing parameters (insulin dosing and/or non-insulin dosing parameters) based on the received glucose measurement and other factors associated with the patient 10, such as risk assessment of hyperglycemic or hypoglycemic effects, demographical information, and clinical biomarkers.

Figure 1C:
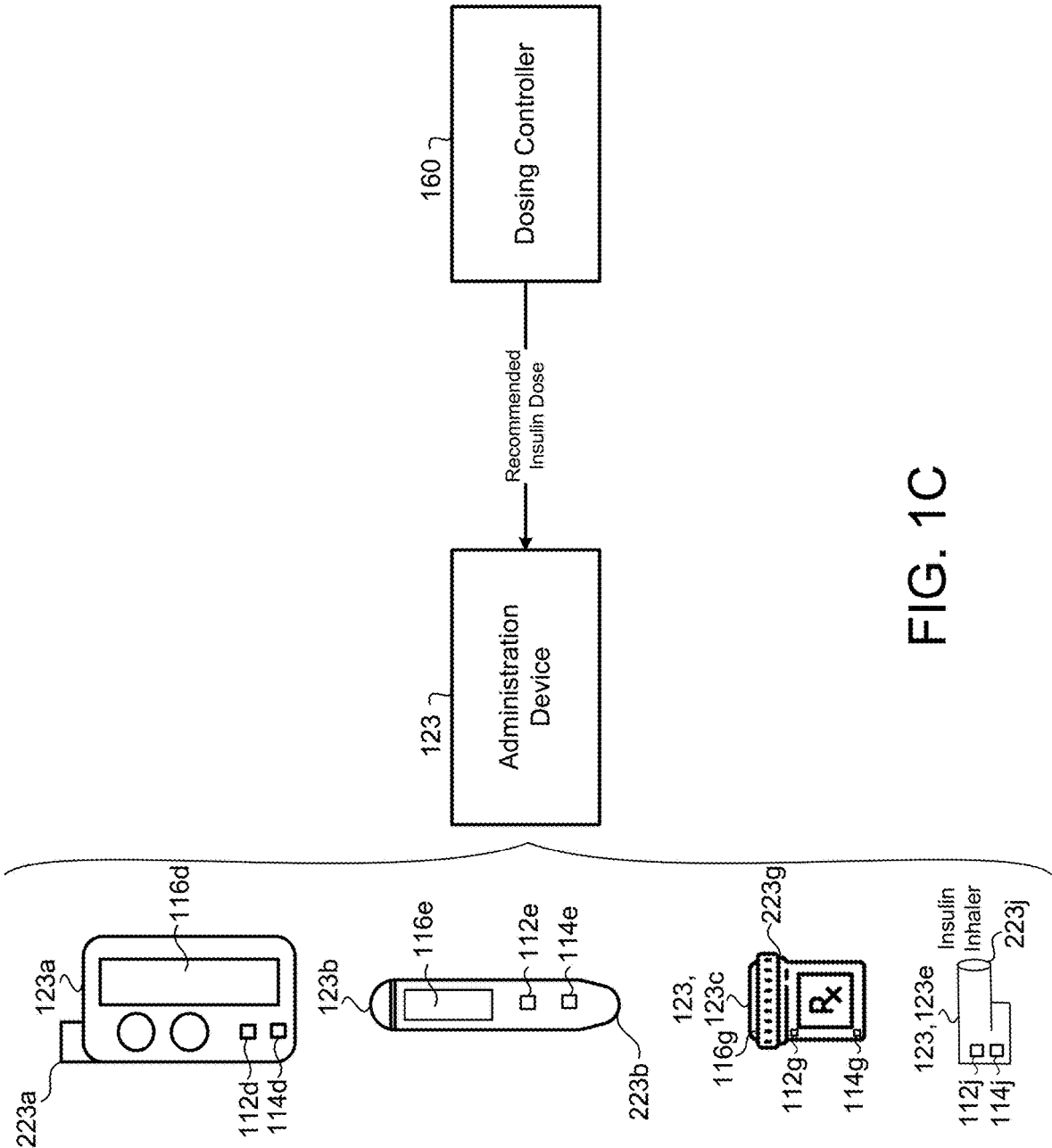
FIG. 1C is a schematic view of an exemplary administration device in communication with a dosing controller.

Referring to FIG. 1C, in some implementations, the administration device 123 (e.g., insulin pen, smart pill bottle/cap, smart pill, insulin inhaler), is in communication with the dosing controller 160, and is capable of executing instructions for administering insulin and/or ADM(s) according to a therapy recommendation generated by the dosing controller 160. The administration device 123 may include the insulin pump 123a, the pen 123b, the smart pill bottle/cap 123c, or the insulin inhaler 123e. The administration device 123 is in communication with the patient devices 110, the glucometer 124, the CGM 127, and the smart scale 125 and includes a computing device 112d, 112e, 112g, 112j and non-transitory memory 114d, 114e, 114g, 114j in communication with the computing device 112d, 112e, 112g. The administration device 123 includes a doser 223a, 223b, 223g, 223j in communication with the administration computing device 112d, 112e, 112g for administering an ADM or insulin to the patient 10. For instance, the doser 223a of the insulin pump 123a includes an infusion set including a tube in fluid communication with an insulin reservoir and a cannula inserted into the patient's 10 body and secured via an adhesive patch. In some examples, the pump 123a may include a patch-based pump that secures to the patient's 10 body via an adhesive, in which the doser 223a includes a cannula or needle inserted into the patient's 10 body. The doser 223b of the pen 123b of the pen 123b includes a needle for insertion into the patient 10 for administering an ADM or insulin to the patient via a cartridge. The doser 223g of the smart pill bottle/cap 123c may include a locking mechanism that unlocks the bottle 123c for administering an ADM pill by the patient 10. Additionally or alternatively, the doser 223g may include a dispensing mechanism that dispenses one or more ADM pills for administering to the patient 10. In some examples, the doser 223g communicates with the display 116g and/or speaker for presenting a visual and/or audio alert to notify the patient 10 it is time to administer a specified dosage of one or more ADM pills. The doser 223j of the insulin inhaler 123e includes a mouthpiece in communication with an insulin cartridge that the patient 10 may insert into his/her mouth for inhaling insulin from the insulin cartridge housed by the insulin inhaler 123e. The administration device 123 may be in communication with the dosing controller 160, and receives instructions from the dosing controller relating to administration of recommended dosages of insulin or ADMs. Here, the administration computing device 112d, 112e, 112g, 112j may execute the therapy recommendation generated by the dosing controller 160 and need not be pre-programmed to execute various anti-diabetes treatment regimens/programs stored within memory 114d, 114e, 114g, 114j, thereby reducing memory usage while increasing processing speeds thereof. Thus, executing the therapy recommendation by administration computing device 112d, 112e, 112g, 112j causes the doser 223a, 223b, 223b, 223g to administer doses of ADMs or insulin specifically tailored for the patient 10 as specified by the therapy recommendation generated for the patient 10. Accordingly, the administration devices 123a, 123b, 123c, 123e may be "smart" administration devices capable of communicating with the dosing controller 160 to populate recommended doses of ADMs or insulin for administering to the patient 10. In some examples, the administration devices 123a, 123b, 123c, 123e execute the dosing controller 160 on the administration computing devices 112d, 112e, 112g, 112j to calculate the recommended doses of ADMs or insulin for administering to the patient 10. Additionally or alternatively, the dosing controller 160 may present recommended dosages of insulin or ADMs for the patient 10 to administer on the display 116 of the patient device 110, thereby enabling the patient 10 to manually enter the recommended dosage of insulin or ADM into the administration device 123.

The network 20 may include any type of network that allows sending and receiving communication signals, such as a wireless telecommunication network, a cellular telephone network, a time division multiple access (TDMA) network, a code division multiple access (CDMA) network, Global system for mobile communications (GSM), a third generation (3G) network, fourth generation (4G) network, Long-Term Evolution (LTE) network, fifth generation (5G) network, a satellite communications network, and other communication networks. The network 20 may include one or more of a Wide Area Network (WAN), a Local Area Network (LAN), and a Personal Area Network (PAN). In some examples, the network 20 includes a combination of data networks, telecommunication networks, and a combination of data and telecommunication networks. The patient device 110, the service provider 130, and the hospital electronic medical record system 140 communicate with each other by sending and receiving signals (wired or wireless) via the network 20. In some examples, the network 20 provides access to cloud computing resources, which may be elastic/on-demand computing and/or storage resources 24 available over the network 20. The term 'cloud' services generally refers to a service performed not locally on a user's device, but rather delivered from one or more remote devices accessible via one or more networks 20.

Figure 1D:
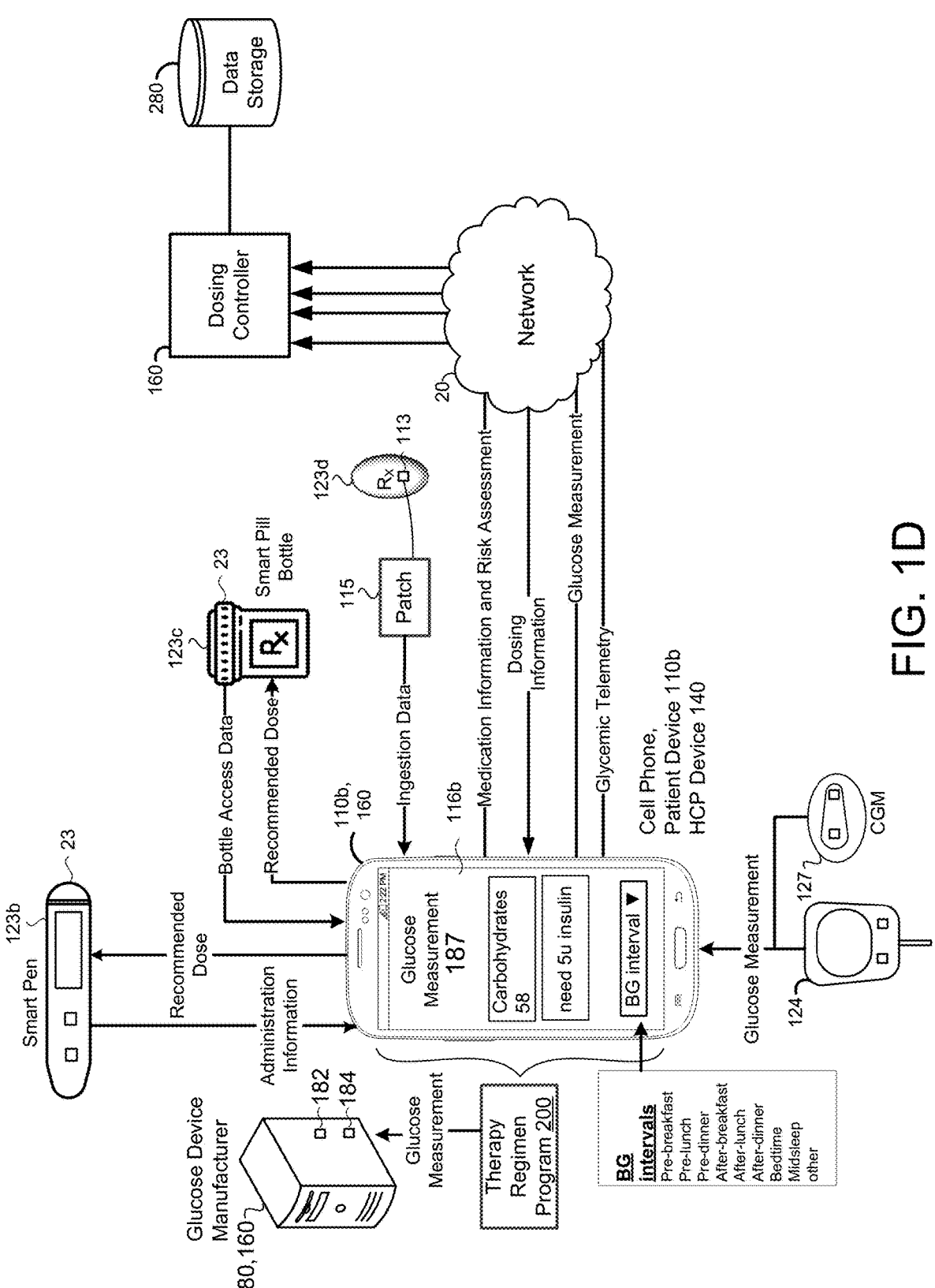
FIGS. 1D and 1E are schematic views of exemplary components of the system of FIGS. 1A-1C.

FIG. 1D is a schematic view of exemplary components of the system 100. In some implementations, the administration device 123 associated with the patient 10 includes a smart pen 123b or smart pill bottle 123c that is capable of communicating (e.g., syncing) with a patient device 110 such as a smart phone 110b. In the example shown, the smart pen 123b and smart pill bottle 123c communicate with the smart phone 110b via Bluetooth, however, other wireless or wired communications are possible. In other examples, the administration device 123 associated with the patient 10 includes the insulin infusion pump 123a and/or insulin inhaler 123e in addition to, or in lieu of, one or more of the smart pen 123b or smart pill bottle 123c. Moreover, the administration device 123 may not be "smart", whereby the patient 10 or user 40 is required to manually enter (e.g., dial in) a recommended dosage of a medication titrated by the dosing controller 160 and displayed on a display 116 of the patient device 110. In some implementations, the dosing controller 160 does not titrate recommended doses for the patient to administer, leaving the responsibility of determining optimal dosages to the HCP 40 or patient 10 for managing glucose levels if the HCP 40 or patient 10 chooses. The smart pen 123b and/or smart pill bottle 123c may include an associated smart cap 23 that removably attaches to the respective smart pen 123*b* or smart pill bottle 123*c*. For instance, the smart cap 23 may attach to the smart pen 123*b* to enclose and protect the doser 223*b* when not being used to administer the ADM or insulin, and then removed from the pen 123*b* to expose the doser 223*b* when the patient 10 is administering and ADM or insulin. Similarly, the smart cap 23 may attach to the smart pill bottle 123*c* to enclose/seal the ADM pills within the smart pill bottle 123*c* and be removed to provide access to the bottle when the patient 10 is administering one or more ADM pills. In some implementations, the smart cap 23 implements some or all of the functionality of the respective smart pen 123*b* or smart pill bottle 123*c*. For instance, the smart cap 23 may include the processor 112*e*, 112*g*, the non-transitory memory 114*e*, 114*g* and/or the display 116*e*, 116*g* instead of the smart pen and smart pill bottle 123*b*, 123*c*, or the pen 123*b* and/or bottle 123*c* may each implement at least one of the processor 112*e*, 112*g* the non-transitory memory 114*e*, 114*g* and/or the display 116*e*, 116*g*. Accordingly, the smart cap 23 may communicate with the patient device 110 (e.g., smart phone 110*b*) via Bluetooth or through other wireless or wired communications.

The glucometer 124 and CGM 127 may also communicate glucose measurements to the smart phone 110*b* via Bluetooth, infrared, cable, or other communications. The program 200 executing on the computing device 112*b* of the smart phone enables the computing device 112*c* to communicate with the dosing controller 160 such that information can be communicated over the network 20 between the dosing controller 160 and each of the smart pill bottle 123*c* (and/or cap 23), smart pen 123*b* (and/or cap 23), the glucometer 124, and the CGM 127. For example, dosing parameters (dosing information) adjusted by the dosing controller 160 may be transmitted to the smart phone 110*b* and stored within memory 114*b* (FIG. 1B). The dosing parameters may include, but are not limited to: TargetBG; target A1c, recommended basal/bolus doses of insulin; recommended ADM doses and types; and scheduled administration times for administering doses of ADMs or insulin. The dosing parameters may be adjusted automatically or manually initiated by the user/HCP 40 or patient 10. Collectively, the dosing information may indicate a therapy recommendation generated by the program.

In some implementations, upon the glucometer 124 or CGM 127 determining a glucose measurement, the glucometer 124 or CGM 127 transmits the glucose measurement to the smart phone 110*b*. The smart phone 110*b* may render the glucose measurement upon the display 116*b* and permit the patient 10 to select the BGtype associated with the glucose measurement. The BGtype or BG Interval corresponds to a label or tag chosen by the patient 10 from a dropdown list upon the display 116*b* of the smart phone 110*b*. Alternatively, the patient 10 may select the BG Interval from a dropdown list displayed on the display 116*c* of the glucometer. The smart phone 110*b* may transmit the glucose measurement and the BG type to the dosing controller 160 via the network 20. In some examples, the glucometer 124 or CGM 127 is configured to transmit the glucose measurement and/or BG type directly to the dosing controller 160 via the network 20. The dosing controller 160 may be configured to store this information in a data storage 280. The patient 10 may also input meal information, such as carbohydrates consumed for breakfast, lunch, or dinner, to the smart phone 110*b*.

The program 200 executing as a mobile application (or other web-based application) may also interface with a proprietary download program executing on the data processor 182 of the glucose device manufacturer provider 180 for uploading glucose measurements measured by the glucometer 124 or CGM 127 and transmitted to the smart phone 110*b*. Here, the glucose device manufacturer provider 180 may authorize and authenticate the dosing controller 160 to retrieve the glucose measurements of the patient 10 stored on the glucose device manufacturer provider 180. Optionally, the glucose measurements may be locally stored on the smart phone 110*b*, but the glucose device manufacturer provider 180 requires the dosing controller 160 to provide appropriate credentials for authorization/authentication to retrieve the glucose measurements from the smart phone 110*b*.

In some examples, the patient 10 may enter a number of carbohydrates for a current meal into the glucometer 124, the CGM 127, or fitness tracker 110*c* for transmission to the smart phone 110*b* or directly into the smart phone 110*b* when a glucose measurement is received. For instance, upon receiving the glucose measurement from the glucometer 124 or the CGM 127, the smart phone 110*b* may render an interactive graphic upon the display 116*b* that enables the patient to enter the number of carbohydrate grams the patient 10 plans to ingest. The program 200 executing on the smart phone 110*b* may provide the glucose measurement and the number of carbohydrate grams to the dosing controller 160 for calculating the recommended dose for display on the display 116*b*.

In some implementations, a recommended dose is determined by the dosing controller 160 and sent to the smart phone 110*b* during each adjustment transmission and stored within the memory 114*b*. The recommended dose may include one or more non-insulin pills/injections or a dosage of insulin for the patient 10 to administer. Accordingly, upon receiving the recommended dose, the mobile application sends the appropriate number of non-insulin pills, doses of non-insulin, or doses of insulin to the administration device 123 and/or presents the recommended dose on the display 116*b* of the smart phone 110*b*. In some examples, the smart pen 123*b* (using the administration computing device 112*e*) automatically dials in the total number of units for the recommended dose of ADM or insulin for the doser 223*b* to administer. The patient 10 may interact with the smart pen 123*b* (or cap 23) or smart pill bottle 123*c* (or cap 23) to accept the recommended dose displayed upon the display 116, 116*e* or manually change the recommended dose. The doser 223*b* of the smart pen 123*b* may include an electromechanical stop that actuates a plunger to only administer the recommended dosage of ADM or insulin accepted by the patient 10 or dosage of ADM or insulin manually entered by the patient 10. Likewise, the doser 223*g* of the smart pill bottle 123*c* may include a locking mechanism that unlocks to dispense a number of ADM pills corresponding to the recommended dosage of ADM. In some examples, upon administration of an ADM or insulin dose by the administration device 123 (e.g., smart pen 123*b* or smart pill bottle 123*c*), the administration device 123 transmits the value of the administered dose (or bottle access data) and the time of the administered dose (or bottle access data) to the smart phone 110*b* for storage within memory 114*b* along with the associated Glucose measurement. Additionally, the smart phone 110*b* may transmit the administered dose (or bottle access data) and the time of the administered dose (or bottle access data) to the dosing controller 160 via the network 20. Here, the patient 10 may explicitly indicate the value (i.e., number of units) of the administered dose and the time that the dose was administered by providing an input to the smart phone 110b. In some configurations, the smart pen 123b (or cap 23) and/or smart pill bottle 123c (or cap 23) forms a direct communication link with the dosing controller 160 via the network 20 for receiving the recommended dosing information and/or transmitting the administered dose and the time of the administered dose to the dosing controller 160.

In some implementations, an ADM pill includes the ADM smart pill 123d that includes the ADM as well as an ingestible sensor 113 that activates when in contact with stomach fluid to detect when the patient 10 administers the pill. Subsequently, the pill is configured to transmit activation by the sensor 113 to a wearable patch 115 (or other transceiver) that transmits the ingestion data to the smart phone 110b. The application 200 executing on the smart phone 110c may log the received ingestion data along with a corresponding time stamp to allow the HCP 40 to access the ingestion data to determine if the patient 10 is being compliant. The patch 115 may include an adhesive for attaching to the patient skin near the stomach, and a transceiver for receiving an indication that the ingestible sensor 113 has been activated upon ingestion and transmitting the ingestion data to the smart phone 110b or other patient device 110. In some examples, if ingestion data is not received by a time threshold for administering the ADM smart pill 123d, the dosing controller 160 may send an alert to the administration device 123 to remind the patient 10 to administer a recommended dosage of the ADM pill 123d in case the patient 10 forgot to administer the pill.

In some implementations, a risk assessment (e.g., via a risk assessment program 300 in FIG. 3A) is determined by the dosing controller 160 and sent to the smart phone 110b and stored within the memory 114b. As will become apparent, the risk assessment is based at least on a tiered glycemic formulary database storing information for a plurality of medications known to affect patient glucose levels. The tiered formulary is organized in ranked tiers based upon the severity and likelihood that a medication will induce a hyperglycemic or hypoglycemic effect on a patient.

In some implementations, communication between the dosing controller 160 and the smart phone 110b enables the HCP 40 to remotely monitor the patient's glycometabolism, past and current glucose levels, as well as other biomarkers and data that are relevant to a patient's glycemic state, as will become apparent.

Figure 1E:
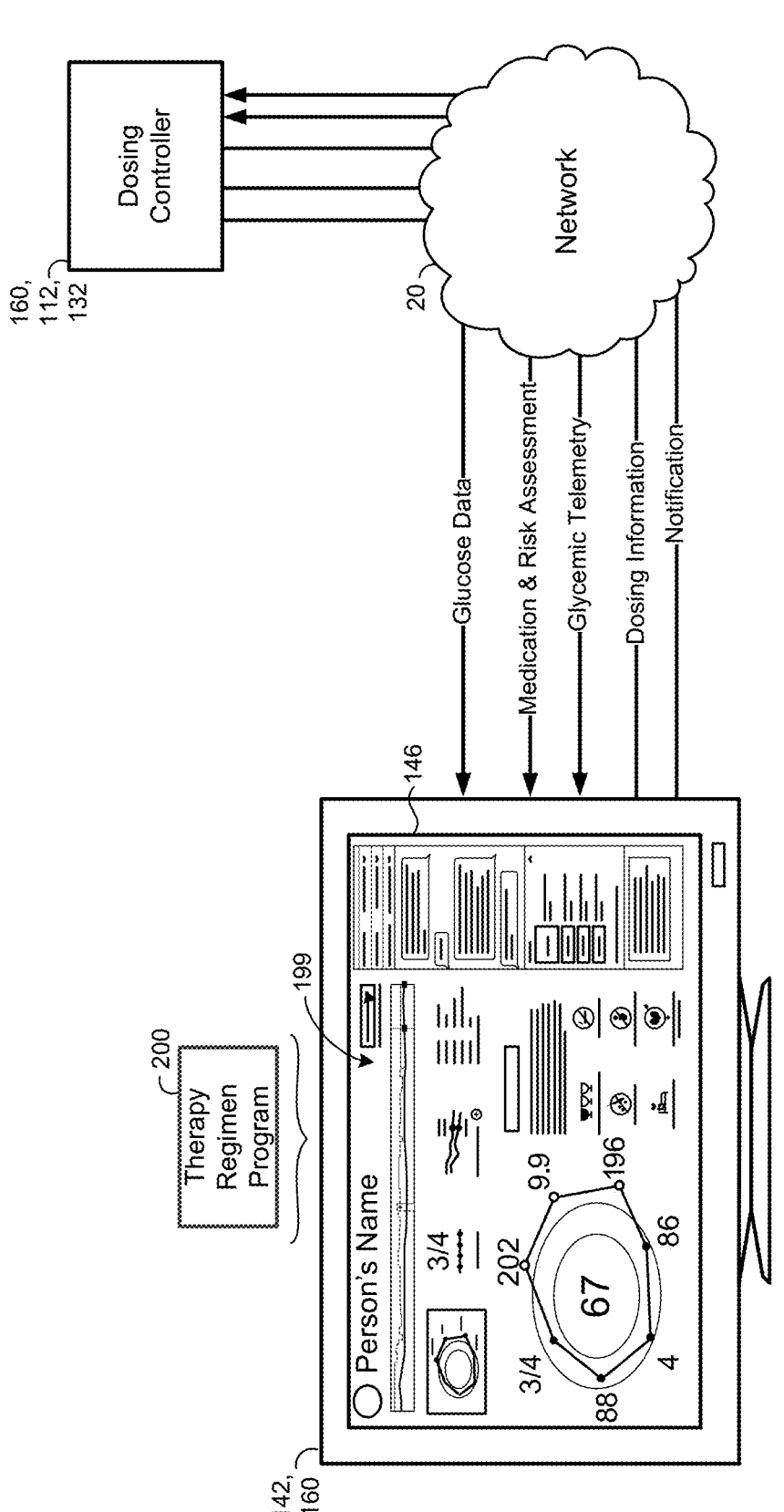

Referring to FIG. 1E, in some implementations, the user device 142 of the clinic system 140 executes the therapy regimen program 200 for communicating with the dosing controller 160 such that information can be communicated over the network 20 between the dosing controller 160 and the user (HCP) device 142. For example, the user device 142 may receive the glucose data, the medication data, and the risk assessment data from the dosing controller 160 via the network 20. In some examples, the computing device 112 of the patient device 110 executes the dosing controller 160 and transmits the glucose data, the medication data and/or the risk assessment data directly to the user device 142. In other examples, the dosing controller 160 executes on the computing device 132 of the service provider 130 such that the computing device 132 receives the glucose data, the medication data and/or the risk assessment data from either one of the patient device 110 or the glucose device manufacturer 180. The service provider 130 may then provide the glucose data, the medication data and/or the risk assessment data to the user device 142. In some scenarios, the glucose device manufacturer 180 includes a propriety download program for downloading and logging glucose measurements measured by the glucometer 124 and/or CGM 127 of the patient 10. Optionally, the manufacture 180 when downloading glucose measurements, may also download time-stamped event data such as when the patient 10 exercised, the type of exercise, the duration of the exercise, when the patient 10 consumed a meal, nutritional data (e.g., number of carbohydrates) for meals consumed by the patient 10, and/or when the patient 10 administered a dose of prescribed medication.

The user device 142 may generate therapy recommendations and update existing therapy recommendations by sending the dosing information to the dosing controller 160 via the network 20 and/or transmit the one or more notifications to the dosing controller 160 for display on a target patient device 110. In some implementations, the therapy regimen program 200 is configured to display on the display screen 146 in communication with the user device 142 a GUI having historical glucose and dosing information 199 for one or more patients 10.

Figure 2A:
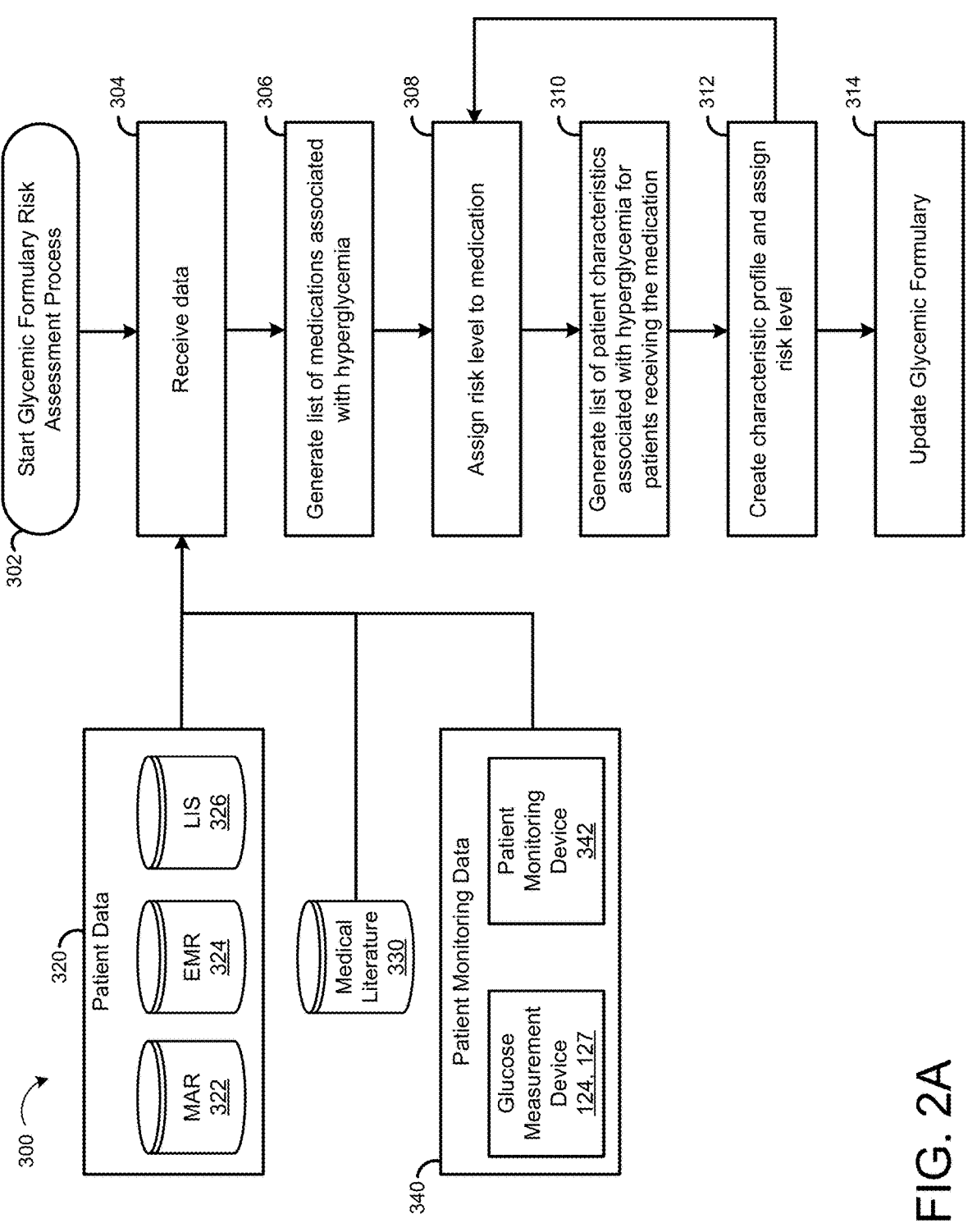
FIG. 2A is a schematic view of an exemplary risk assessment program of the system of FIGS. 1A-1C.

Referring to FIG. 2A, the therapy regimen program 200 may evaluate and select medications to be included in a therapy recommendation based on the risk assessment program 300 executed by the dosing controller 160. The risk assessment program 300 begins at operation 302. At operation 304, the dosing controller 160 receives a plurality of data, including patient data 320, medical literature 330, and patient monitoring data 340. The patient data 320 may include the patient's medical administration record (MAR) 322, the patient's electronic medical record (EMR) 324, and the patient's laboratory information system (LIS) 326. The patient data 320 includes the medications that the patient 10 is taking, any diseases or disorders that the patient 10 has, and historical medical information associated with the patient 10. The medical literature 330 includes, e.g., peer-reviewed articles, federal guidelines, and any other suitable literature. As just one example, the medical literature may indicate what medications are known to cause hyperglycemic effects on a typical patient. The patient monitoring data 340 includes the glucose measurement device 124, 127 and a patient monitoring device 342. The patient monitoring device 342 comprises any suitable device capable of obtaining biomedical data associated with the patient 10, including, but not limited to: the personal computer 110, 110a of the patient 10; the patient device 110, 110b (e.g., mobile phone, tablet); the smart wearable 110, 110c (e.g., smart watch, fitness tracker); the insulin pump 123, 123a; the smart pen 123, 123b; the smart pill bottle 123c; the smart pill 123d configured to detect and communicate ingestion; the insulin inhaler 123e; the glucometer 124; the CGM 127; the body weight scale 125, the HCP device 140; the service provider 130; a Holter monitor; a blood pressure monitor; a cholesterol meter or monitor; a blood glucose meter or monitor; an electrocardiograph (ECG or EKG) monitor or machine; a heart rate monitor; an exercise or activity monitor; a gamma camera; a fluoroscope; an X-ray machine; a spirometer; a pulse oximeter; a capnography monitor; a blood test machine; a breathalyzer; a tactile sensor; a sleep sensor; a gyroscope; a fall-detection sensor; an oxygen saturation sensor; a camera; an infrared camera; and an infrared sensor.

At operation 306, the dosing controller 160 generates a list of medications associated with hyperglycemia. As just one example, dexamethasone is a potent glucocorticoid known to cause hyperglycemia in as many as half of patients receiving the medication. At operation 308, the dosing controller 160 assigns a risk level to each of the medications. Continuing with the example, dexamethasone would be classified in the high-risk tier in the glycemic formulary. At operation 310, the dosing controller 160 generates a list of patient characteristics associated with hyperglycemia for patients receiving the medication. Continuing with the example, patients who receive a high dose of dexamethasone, who are older, tend to have a high hemoglobin A1C and an elevated BMI are at a high-risk of experiencing hyperglycemia. At operation 312, the dosing controller 160 creates a characteristic profile and assigns a risk level to the profile. Continuing with the example, a characteristic profile for a patient receiving a high dose of dexamethasone, are older, have a high hemoglobin A1C and an elevated BMI would be assigned a high risk level for hyperglycemia. The dosing controller 160 may return to operation 308 if the characteristic profile impacts the risk level assigned to medication. For example, if the dosing controller 160 determines that a certain medication is associated with multiple characteristic profiles experiencing hyperglycemia, then the dosing controller 160 may modify the risk level assigned to this medication at operation 308 to increase the risk level. At operation 314, the dosing controller 160 updates the glycemic formulary to determine the severity and likelihood that a medication will induce a hyperglycemic or hypoglycemic effect on the patient 10.

Figure 2B:
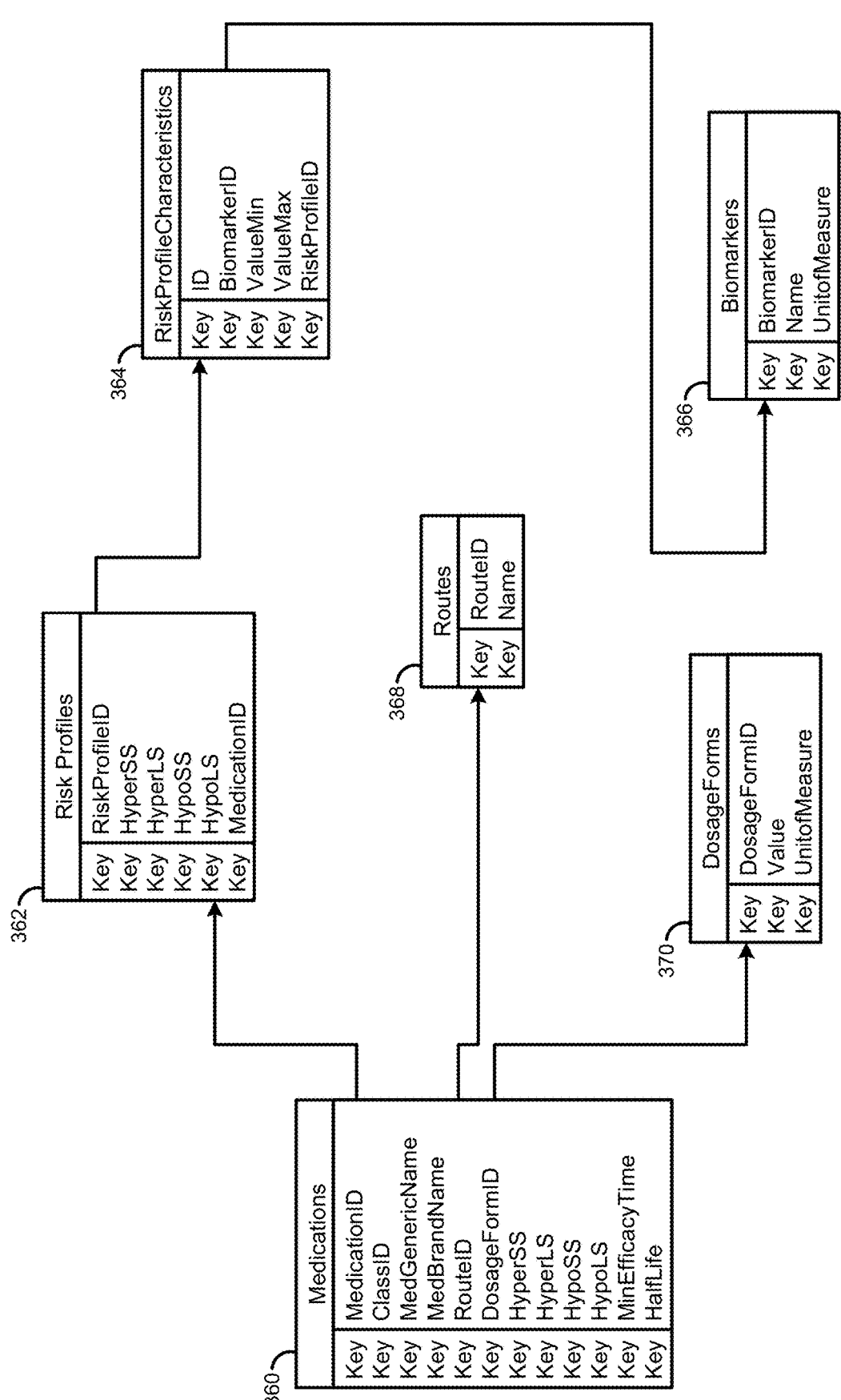

Referring to FIGS. 2B and 2C, the risk assessment program 300 considers a variety of information to determine the determine the severity and likelihood that a medication will induce a hyperglycemic or hypoglycemic effect on the patient 10. Such information includes, but is not limited to: medication data 360, risk profile data 362, risk profile characteristics data 364, biomarkers data 366, routes data 368, and dosage forms data 370. As shown in FIG. 2B, the medication data 360 includes keys such as MedicationID, ClassID, MedGenericName, MedBrandName, RouteID, DosageFormID, HyperSS, HyperLS, HypoSS, HypoLS, MinEfficacy Time, and HalfLife. The risk profiles data 362 includes keys such as RiskProfileID, HyperSS, HyperLS, HypoSS, HypoLS, and MedicationID. The risk profile characteristics data 364 includes keys such as ID, BiomarkerID, ValueMin, ValueMax, and RiskProfileID. The biomarkers data 366 includes keys such as BiomarkerID, Name, and UnitofMeasure. The routes data 368 includes keys such as RouteID and Name. The dosage forms data 370 includes keys such as DosageFormID, Value, and UnitofMeasure.

Referring to FIG. 2C, an exemplary set of data is illustrated, including a first exemplary set of medication data 360, 360a, a first exemplary set of risk profile data 362, 362a, a first exemplary set of risk profile characteristics data 364, 364a, and a first exemplary set of biomarkers data 366, 366a. As can be seen in FIG. 2C, the exemplary medication data 360, 360a includes three medications: two different brand names of methylprednisolone and atenolol. The exemplary risk profile data 362, 362a corresponds to MedicationID 1: methylprednisolone sold under the brand name SOLU-MEDROL®. The exemplary risk profile characteristics data 364, 364a includes data for three biomarkers corresponding to age, HbA1C, and BMI, as indicated by the exemplary biomarker data 366, 366a.

Figure 3:
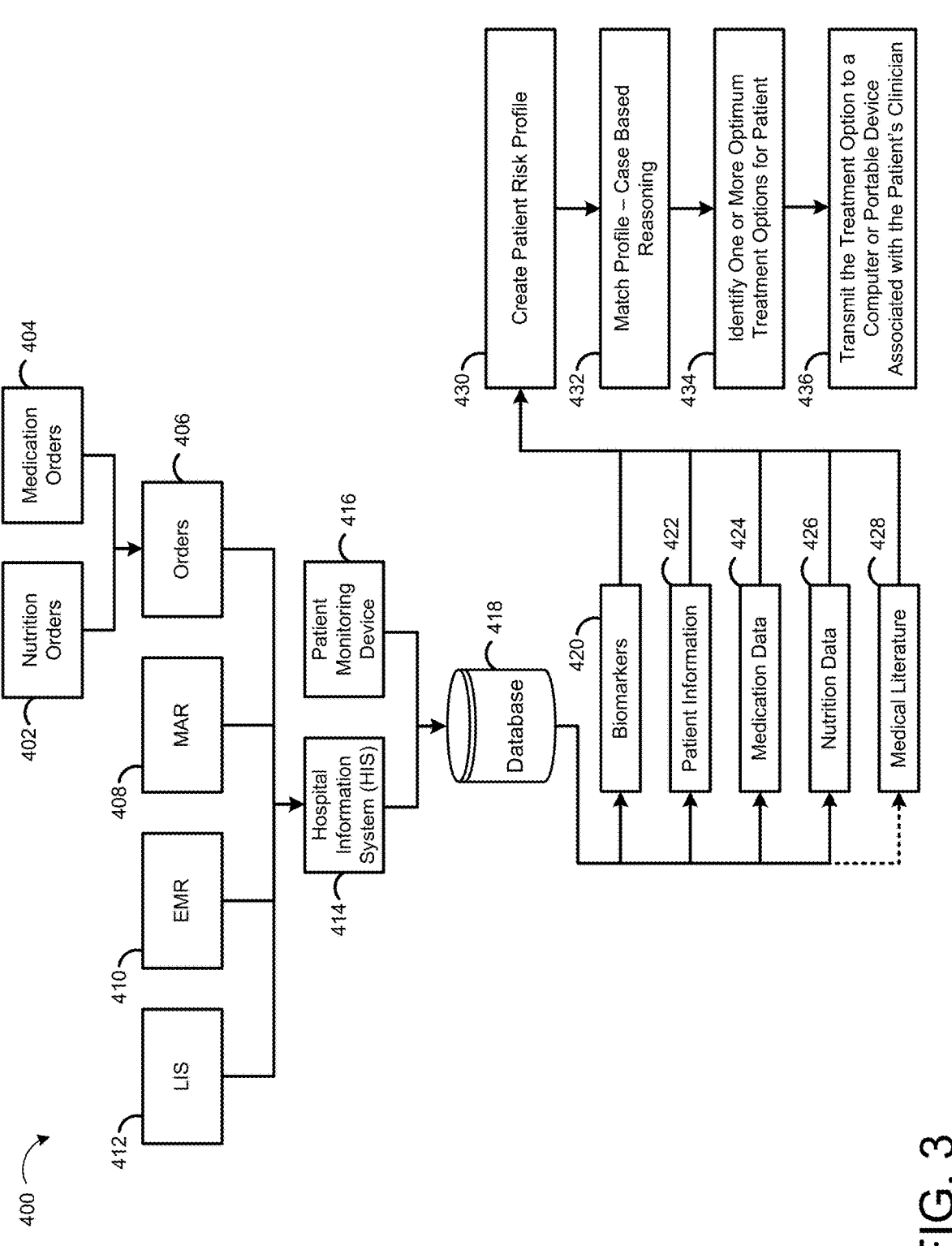
FIG. 3 is a schematic view of an exemplary glycemic telemetry program of the system of FIGS. 1A-1C.

Referring to FIG. 3, the clinical support system 100 includes a glycemic telemetry program 400 executed by the dosing controller 160. The glycemic telemetry program 400 enables a HCP 40 to remotely monitor a patient's 10 glycometabolism, past and current glucose levels, as well as other biomarkers and data that are relevant to a glycemic state of the patient 10. At operation 402, nutrition order data is obtained, and at operation 404, medication order data is obtained. At operation 406, the nutrition order data and the medication order data is received by the dosing controller 160. The nutrition order data and the medication order data may be obtained in any suitable manner, including being manually entered by the HCP 40 or the patient 10, or being automatically obtained by the dosing controller 160 in communication with other computing devices, third-party software, or any other suitable sources. At operation 408, the patient's MAR data is obtained. At operation 410, the patient's EMR data is obtained. At operation 412, the patient's LIS data is obtained. The MAR data, the EMR data, and the LIS data may be obtained in any suitable manner, including being manually entered by the HCP 40 or the patient 10, or being automatically obtained by the dosing controller 160 in communication with other computing devices, third-party software, or any other suitable sources. At operation 414, the hospital information system (HIS) obtains the nutrition order data, the medication order data, the MAR data, the EMR data, and the LIS data and stores it in a database at operation 418. At operation 416, the patient monitoring device 342 obtains patient data and stores it in the database in operation 418. As described herein, the patient monitoring device 342 comprises any suitable device capable of obtaining biomedical data associated with the patient 10.

The database 418 includes biomarkers 420, patient information 422, medication data 424, nutrition data 426, and, in some implementations, medical literature 428. The biomarkers 420 may include continuous glucose monitoring data, point-of-care capillary or venous blood glucose measurements, height, weight, anion gap, potassium, pH, bicarbonate, osmolality, sodium, blood urea nitrogen, triglycerides, blood pressure, oxygen saturation, glomerular filtration rate, creatinine, albumin, and hemoglobin A1c, etc. The patient information 422 includes patient demographical information such as age, gender, history of diabetes, ethnicity, prior inpatient glycemic treatment history, as well as type and dosage of any diabetes medications taken at home. The medication data 424 includes the drug name, dosage, route of administration, frequency, and datetime of administration of any medications known to impact patient blood glucose levels, such as glucocorticoids and protease inhibitors. The nutrition data 426 includes information related to the patient's eating habits, including, but not limited to, food allergies, food sensitivities, average caloric intake, and personal nutrition choices such as vegetarian, vegan, etc. The medical literature 428 may be stored in the database 418, or the medical literature 428 may be stored in a remote server or obtained via any suitable means. The medical literature 428 includes, e.g., peer-reviewed articles, federal guidelines, and any other suitable literature.

At operation 430, the dosing controller 160 creates a patient risk profile for the specific patient 10 based on the biomarkers 420, the patient information 422, the medication data 424, the nutrition data 426, and the medical literature 428. At operation 432, the dosing controller 160 matches the specific patient risk profile with one of a plurality of patient risk profiles curated from historical data derived from the treatment of other patients with similar profiles to the specific patient. By using historical data from several other patients, the dosing controller 160 may use predictive reasoning based on similar patient profiles to determine one or more optimum treatment options for the patient at operation 434. For example, if a past patient with a similar risk profile to the current patient is given a certain treatment, the dosing controller 160 has the benefit of understanding the impact that that treatment had on that past patient, and use the data from that past patient to predict how the current patient will react to the same or similar treatment. In other implementations, the dosing controller 160 may determine an optimal treatment plan using any suitable method or algorithm, such as a therapy selection program 500 in FIG. 4. At operation 436, the dosing controller 160 transmits the treatment option to the HCP device 140 or, in some implementations, to the patient device 110 or patient administration device 123.

Figure 4:
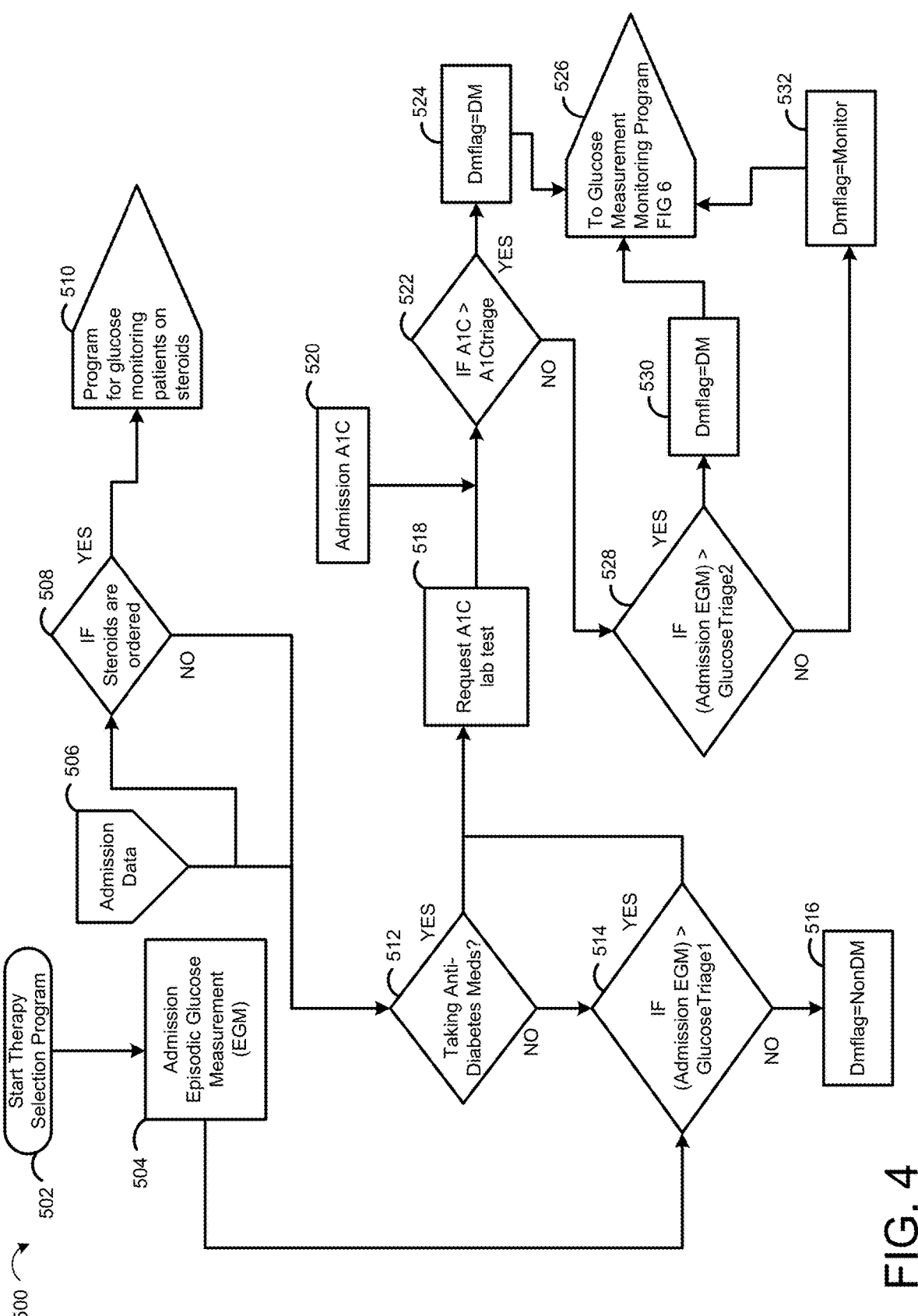
FIG. 4 is a schematic view of an exemplary therapy selection program of the system of FIGS. 1A-1C.
Figure 6:
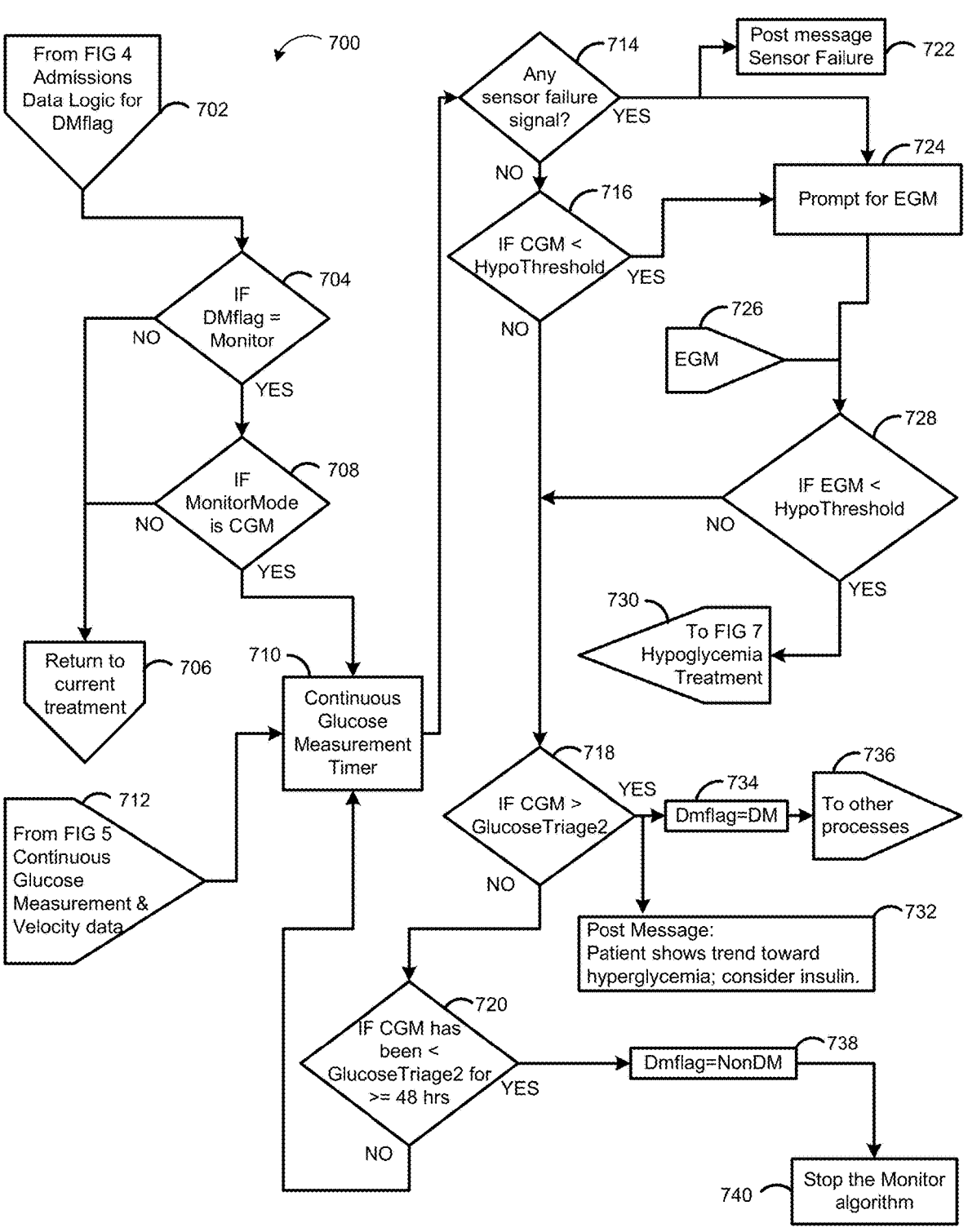
FIG. 6 is a schematic view of an exemplary continuous glucose measurement program of the system of FIGS. 1A-1C.

Referring to FIG. 4, the therapy selection program 500 is generally shown, whereby the program 500 is executed by the dosing controller 160 and starts at operation 502. At operation 504, a glucose measurement of the patient 10 is determined based on, e.g., an episodic glucose measurement (EGM), for example a glucose meter measurement, a point of care glucose measurement (POC), or any other suitable measurement that is tested episodically. At operation 506, admission data associated with the patient 10 is obtained. The admission data may be manually entered by the HCP 40 and/or the patient 10 or the admission data may be obtained in any suitable manner. At operation 508, the dosing controller 160 determines whether steroids are ordered. If the dosing controller 160 determines that steroids are ordered, then the therapy selection program 500 proceeds to operation 510 to execute a program for glucose monitoring patients on steroids. If the dosing controller 160 determines that steroids are not ordered, then the therapy selection program 500 proceeds to operation 512 where the dosing controller 160 determines whether the patient 10 is taking anti-diabetes medications based on the admission data 506. At operation 514, if the admission glucose measurement obtained at operation 504 is less than GlucoseTriage1, then the dosing controller 160, at operation 516, identifies DMflag as NonDM, i.e., Diabetes Mellitus (DM) is unlikely. If, at operation 512, the patient is taking anti-diabetes medications and/or if, at operation 514, the admission glucose measurement obtained at operation 504 is greater than GlucoseTriage1, then the dosing controller 160 requests an A1C lab test at operation 518. At operation 520, the therapy selection program 500 obtains the patient's 10 admission A1C. The admission A1C may be manually entered by the HCP 40 and/or the patient 10 or the admission A1C may be obtained in any suitable manner. At operation 522, the dosing controller 160 determines whether the admission A1C is greater than or less than A1Ctriage. If the admission A1C is greater than A1Ctriage, then the dosing controller 160, at operation 524, identifies DMflag as DM, i.e., DM is likely, and proceeds to a glucose measurement monitoring program 700 at operation 526. If the admission A1C is less than A1Ctriage, then the dosing controller 160, at operation 528, determines whether the admission glucose measurement is greater than or less than GlucoseTriage2. If the dosing controller 160 determines that the admission glucose measurement is greater than GlucoseTriage2, then the dosing controller 160, at operation 530, identifies DMflag as DM, i.e., DM is likely, and proceeds to the glucose measurement monitoring program 700 at operation 526. If the dosing controller 160 determines that the admission glucose measurement is less than GlucoseTriage2, then the dosing controller 160, at operation 532, identifies DMflag as Monitor, i.e., DM is possible and the patient 10 should be monitored for DM, and proceeds to the glucose measurement monitoring program 700 at operation 526, as shown in FIG. 6.

In the therapy selection program 500, there are three configurable constants: A1Ctriage, GlucoseTriage1, and GlucoseTriage2. As just one example, A1Ctriage may be equal to 6.5, GlucoseTriage1 may be equal to 140, and GlucoseTriage2 may be equal to 180. The parameter DMflag may be linked with the patient 10 through his/her hospital stay. DMflag is initially assigned by the therapy selection program 500 which runs immediately after the patient's 10 admission, but DMflag may be changed by other programs later in the patient's 10 hospital stay.

Figure 5:
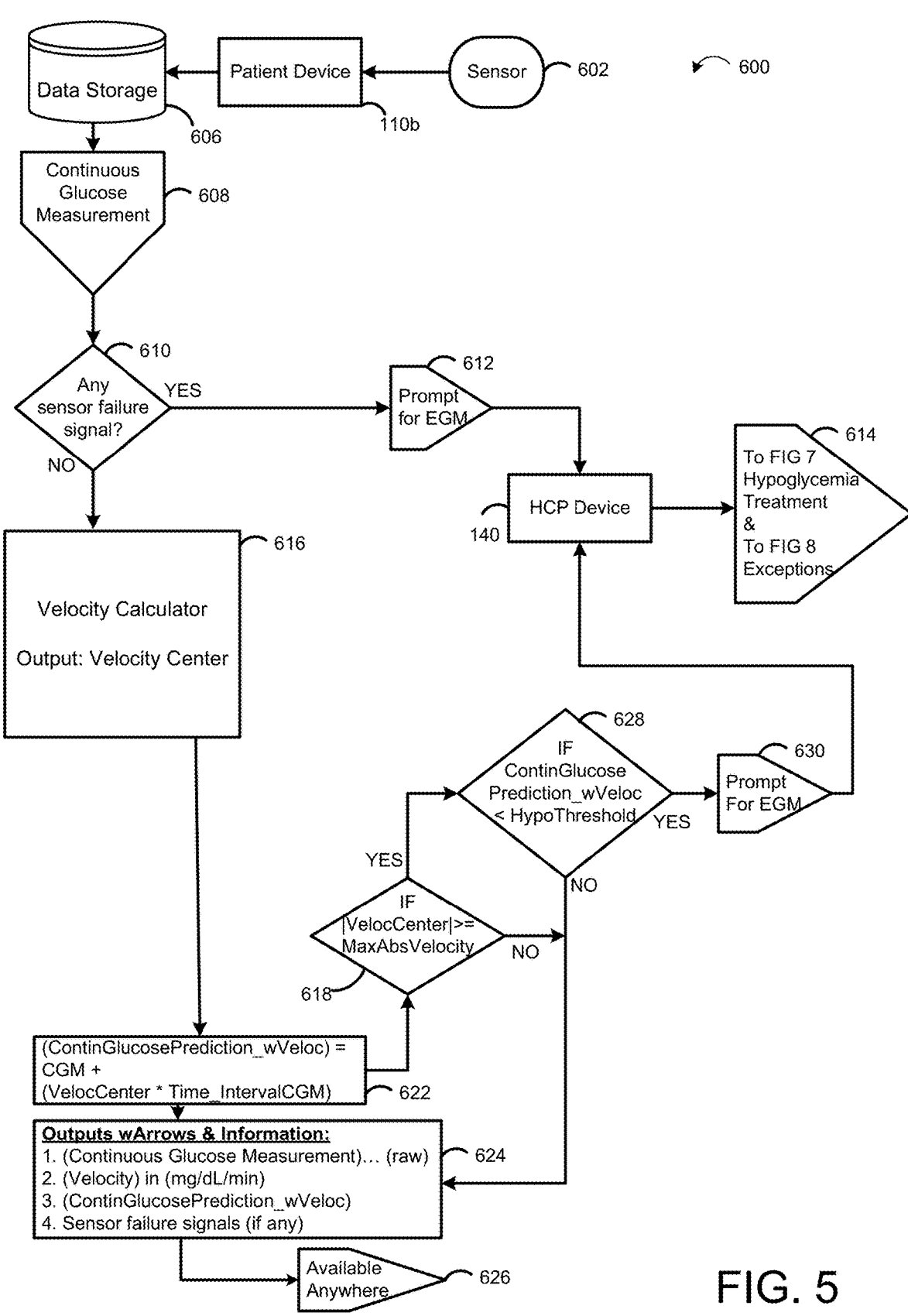
FIG. 5 is a schematic view of an exemplary continuous glucose measurement program using trend velocity of the system of FIGS. 1A-1C.

Referring to FIG. 5, a continuous glucose measurement trend Veloc program 600 is generally shown, whereby the program 600 is executed by the dosing controller 160 and starts at operation 602 where continuous glucose measurement data is obtained from the CGM sensor 127 or any other suitable device. The continuous glucose measurement data is transmitted from the CGM sensor 127 to a portable device at operation 604, where the portable device may include the patient device 110b and/or any other suitable device. The portable device sends the CGM data to Data Storage 606, which may be an on-site database or in the cloud. The stored data may include continuous Glucose Measurement (CGM) data, certain criteria to determine, e.g., sensor failure, glucose velocity, velocity-indicating codes, etc. At operation 608, the dosing controller 160 obtains the continuous glucose measurement data from data storage 606; this data may be obtained by wired, co-axial, fiber optic, WiFi, Cellular Network, Bluetooth, or any suitable wired or wireless transmission method.

At operation 610, the dosing controller 160 analyzes the received continuous glucose measurement to determine whether there is any sensor failure signal. If the dosing controller 160 determines that there is sensor failure, then, at operation 612, the dosing controller 160 sends a prompt to the patient device 110 and/or the HCP device 140 for the patient 10 or HCP 40 to conduct an EGM. At operation 614, the program 600 proceeds to the programs set forth in FIG. 7 and FIG. 8 for hypoglycemia treatment and to determine if a comparison of CGM to EGM shows any exceptions to published criteria. If, at operation 610, the dosing controller 160 determines that there is not any sensor failure, then the data is sent to exemplary CGM Translator at operation 616, where these translators are exemplary for an exemplary CGM sensor brand. These translators 616 may be tables or sets of formulas. At 616 the glucose velocity-based data, signals, or codes are construed in a manner appropriate for the exemplary CGM data.

As shown in FIG. 5, exemplary translator 616 is shown calculating, glucose velocities or relating velocity codes to velocities for an exemplary CGM sensor brand, but it should be understood that different data sets may be available based on different sensor manufacturers, and therefore different methods may be implemented for obtaining CGM velocities or central velocities for velocity ranges.

The dosing controller 160 sends information from translator 616 to operation 622 where ContinGlucosePrediction_wVelocity is calculated using the following equation:

$$\text{ContinGlucosePrediction\_}_w\text{Velocity=Continuous Glucose Measurement+ Velocity*Timer\_IntervalCGM} \qquad (1)$$

where Timer_IntervalCGM is based on the sensor manufacturer data, and the maximum allowable glucose velocity in the dosing controller 160, and may be equal to between 1 min and 30 min, with a suggested value of 15 min. At operation 624, the dosing controller 160 generates the following data: Continuous Glucose Measurement, Glucose_Velocity, ContinGlucosePrediction_wVelocity, and a notification of any sensor failure. At operation 626, the dosing controller 160 makes the foregoing data digitally available to any process that may need it. At operation 618, if the dosing controller 160 determines that the value of the absolute value of the velocity, which may be calculated directly or in some embodiments as the absolute value of the center of a velocity range, (VelocCenter) is less than a configurable limit (MaxAbsVelocity) then no action is taken except the data is sent to the output operation 624. If, at operation 618, the dosing controller 160 determines that the velocity or in some embodiments the center of the velocity range, is greater than or equal to the configurable limit (MaxAbsVelocity), then the data and logic are sent to operations 628 and 624. At operation 628, the dosing controller 160 determines whether ContinGlucosePrediction_wVelocity is less than HypoThreshold, whereby HypoThreshold may be, e.g., between 50 and 100 mg/dL, with a suggested value of 70 mg/dL. If, at operation 628, the dosing controller 160 determines that ContinGlucosePrediction_wVelocity is greater than HypoThreshold, then the program 600 proceeds to operation 624. If, at operation 628, the dosing controller 160 determines that ContinGlucosePrediction_wVelocity is less than HypoThreshold, then, at operation 630, the dosing controller 160 executes a prompt for the patient 10 or HCP 40 to conduct an EGM, where the HCP receives the prompt at the HCP Device 140, and at operation 614, the program 600 proceeds to the programs set forth in FIG. 7 and FIG. 8 for hypoglycemia treatment and to determine if there are any exceptions, respectively. In some implementations, a configurable constant, PlateauAbsVeloc, may be equal to 1.0 mg/dL/min or 60 mg/dL/hr.

Referring to FIG. 6, a continuous glucose measurement monitoring program 700 is generally shown, whereby the program 700 is executed by the dosing controller 160 and starts at operation 702 from operation 526 of the therapy selection program 500, as shown in FIG. 4. Specifically, at operation 702, the dosing controller 160 obtains admission data logic for DMflag, and, at operation 704, the dosing controller 160 determines whether DMflag=monitor. If the dosing controller 160 determines that DMflag does not equal monitor, then the program 700 returns to the current treatment for the patient 10 at operation 706. If, at operation 704, the dosing controller 160 determines that DMflag does equal monitor, then the dosing controller 160, at operation 708, determines whether the monitor mode is continuous glucose monitoring: if no, the program 700 returns to the current treatment for the patient 10 at operation 706; and if yes, the dosing controller 160 proceeds to the continuous glucose measurement timer at operation 710. At operation 710, the dosing controller 160 obtains the continuous glucose measurement data from the manufacturer's cloud-based database, which is provided at operation 712 from the continuous glucose measurement trend Veloc program 600, as shown in FIG. 5.

At operation 714, the dosing controller 160 determines whether there is any sensor failure signal. If the dosing controller 160 determines that there is not any sensor failure signal, then the program 700 proceeds to operation 716, where the dosing controller 160 determines whether the continuous glucose measurement is less than a pre-determined hypoglycemia threshold (HypoThreshold). If the dosing controller 160 determines that the continuous glucose measurement is greater than the pre-determined hypoglycemia threshold, then the program 700 proceeds to operation 718, where the dosing controller 160 determines whether the continuous glucose measurement is greater than a pre-determined GlucoseTriage2. If the dosing controller 160 determines that the continuous glucose measurement is less than the pre-determined GlucoseTriage2, then the program 700 proceeds to operation 720, where the dosing controller 160 determines whether the continuous glucose measurement has been less than the pre-determined GlucoseTriage2 for 48 hours or more. If the dosing controller 160 determines that the continuous glucose measurement has not been less than the pre-determined GlucoseTriage2 for 48 hours or more, the program 700 proceeds to the continuous glucose measurement timer at operation 710.

Figure 7:
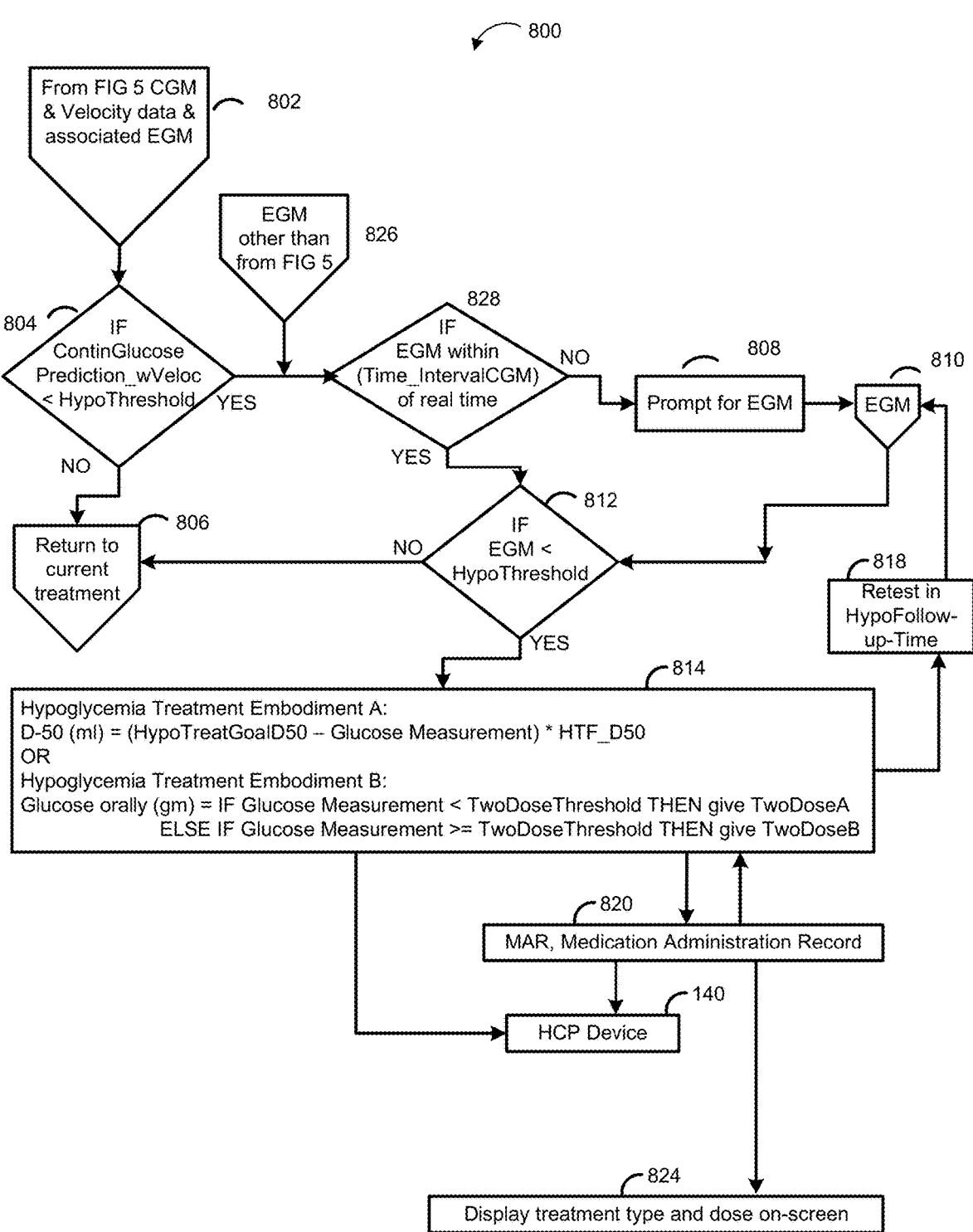
FIG. 7 is a schematic view of an exemplary hypoglycemia treatment program of the system of FIGS. 1A-1C.

If, at operation 714, the dosing controller 160 determines that there is a sensor failure signal, then the dosing controller 160, at operation 722, displays message "Sensor Failure" at one or more of the patient device 110, the HCP device 140, and/or the service provider 130, and executes a prompt for the patient 10 or HCP 40 to conduct an EGM. At operation 726, the dosing controller 160 obtains the EGM, and at operation 728, the dosing controller 160 determines whether the EGM is less than the pre-determined hypoglycemia threshold. If the dosing controller 160 determines that the EGM is greater than the pre-determined hypoglycemia threshold, then the program 700 proceeds to operation 718. If, at operation 728, the dosing controller 160 determines that the EGM is less than the pre-determined hypoglycemia threshold, then the dosing controller 160 proceeds to a hypoglycemia treatment program 800, as shown in FIG. 7, at operation 730. If, at operation 716, the dosing controller 160 determines that the continuous glucose measurement is less than the pre-determined hypoglycemia threshold, then the program 700 proceeds to operation 724. If, at operation 718, the dosing controller 160 determines that the continuous glucose measurement is greater than the pre-determined GlucoseTriage2, then the program 700 proceeds to operation 732 where the dosing controller 160 displays message "Patient shows trend toward hyperglycemia; consider insulin" at one or more of the patient device 110, the HCP device 140, and/or the service provider 130. At operation 734, the dosing controller 160 changes DMflag to DMflag=DM and proceeds to other processes to manage diabetes mellitus at operation 736. If, at operation 720, the dosing controller 160 determines that the continuous glucose measurement has been less than the pre-determined GlucoseTriage2 for 48 hours or more, the program dosing controller 160 identifies DMflag-NonDM at operation 738, and stops the program 700 at operation 740.

Referring to FIG. 7, a hypoglycemia treatment program 800 is generally shown, whereby the program 800 is executed by the dosing controller 160 and starts at operation 802 from operation 614 of the continuous glucose measurement using trend velocity program 600, as shown in FIG. 5 with an associated EGM. At operation 826 EGM measurements from other locations in the software enter the process. At operation 828 it is determined if any of the EGM measurements were measured within one (Time_IntervalCGM) of the current time. At operation 804, the dosing controller 160 determines if ContinGlucosePrediction_wVelocity is less than a pre-determined hypoglycemia threshold. If no, the program 800 returns to the current treatment for the patient 10. If, at operation 804, the dosing controller 160 determines that ContinGlucosePrediction_wVelocity is less than the pre-determined hypoglycemia threshold, then the dosing controller 160 proceeds to 826 where EGM measurements from other locations in the software enter the process. At operation 828, the dosing controller 160 determines if any of the EGM measurements were measured within one (Time_IntervalCGM) of the current time. If no, then the dosing controller 160 executes a prompt for an EGM check at operation 808 and obtains the EGM check at operation 810.

At operation 812, the dosing controller 160 determines whether any of the EGM checks is less than the hypoglycemia threshold. If no, the program 800 returns to the current treatment for the patient 10 at operation 806. If, at operation 812, the dosing controller 160 determines that an EGM check is less than the hypoglycemia threshold, then the program 800 proceeds to operation 814, where exemplary hypoglycemia treatments are shown using one of the following equations:

$$[D - 50 \text{ (ml)}] = \tag{2}$$
$$(HypoTreatGoalD50 - \text{Glucose Measurement}) * HTF_{D50}$$

Glucose orally (gm) = IF Glucose Measurement < *TwoDoseThreshold* (3)

THEN give *TwoDoseA*

ELSE IF Glucose Measurement ≥ *TwoDoseThreshold*

THEN give *TwoDoseB* where HypoTreatGoalD50 is suggested to be 120, $HTF_{D50}$ is suggested to be 0.4 ml/(mg/dL), TwoDoseA is suggested to be 15 gm, TwoDoseB is suggested to be 30 gm, and TwoDoseThreshold is suggested to be 55 mg/dL. In other implementations, Equation 2 may substitute HypoTreat-GoalD50 with HypoTreatGoalOral and $HTF_{D50}$ with $HTF_{oral}$ for oral medication, in which HypoTreatGoalOral is suggested to be 120 and $HTF_{oral}$ is suggested to be 0.2 gm/(mg/dL).

At operation 818, the dosing controller executes a prompt to retest in HypoFollow-up-Time, which may be equal to 15 min, and returns to operation 810. The hypoglycemia treatment from operation 814 is transmitted to the HCP device 140 at operation 822. In some implementations, the hypoglycemia treatment from operation 814 is transmitted to the Medication Administration Record (MAR) at operation 820. At operation 826, the dosing controller 160 displays the treatment type and dose from operation 814 on one or more of the patient device 110, the HCP device 140, and/or the service provider 130 at operation 824.

Figure 8:
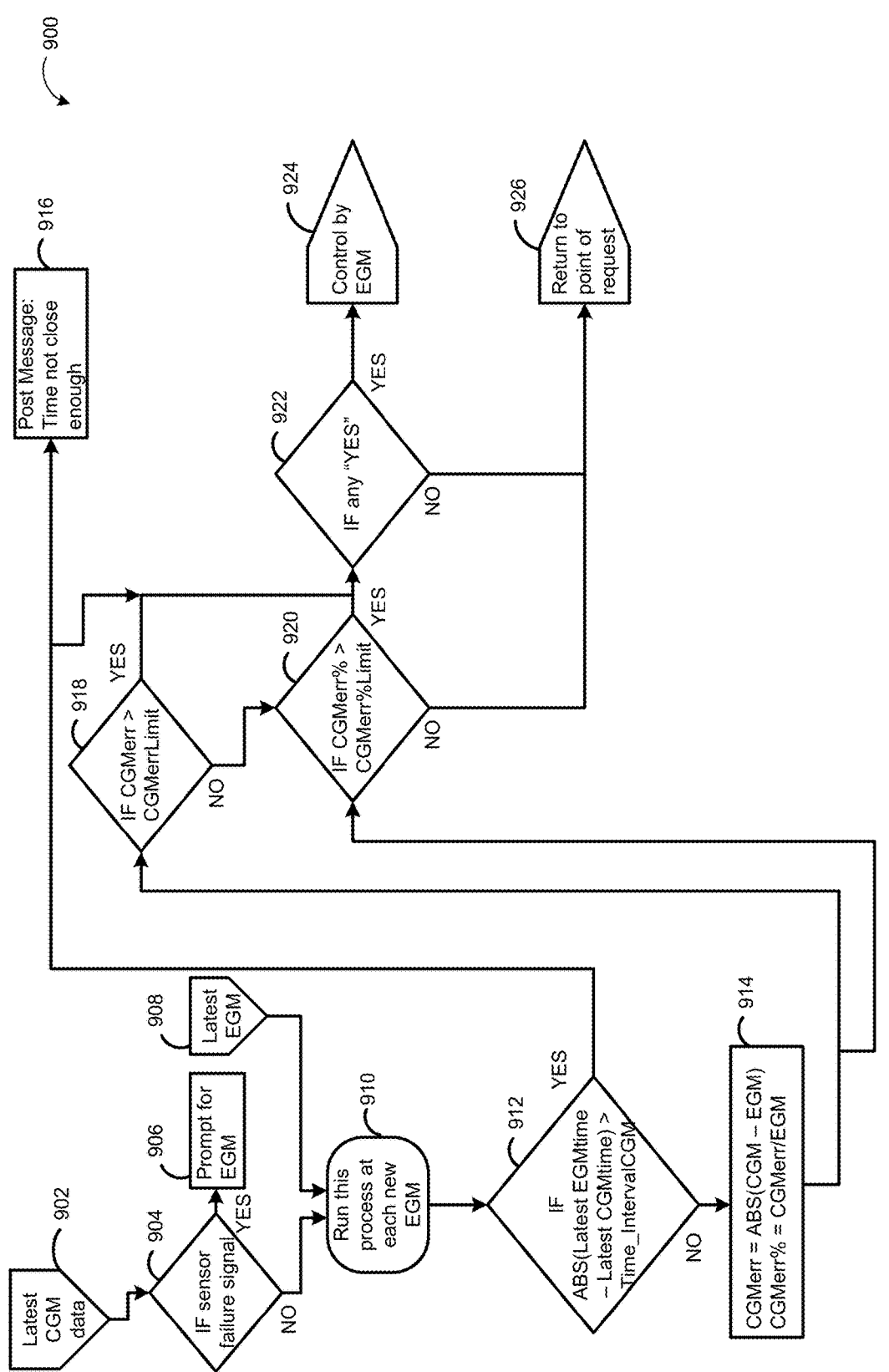
FIG. 8 is a schematic view of an exemplary comparison exceptions and reference check program of the system of FIGS. 1A-1C.

Referring to FIG. 8, a comparison exceptions program 900 is generally shown, whereby the program 900 is executed by the dosing controller 160 and starts at operation 908 where the dosing controller 160 obtains the latest EGM. At operation 910, the dosing controller 160 runs the program 900 every time there is a new EGM, where new is defined as within 2*(Time_IntervalCGM). At operation 902, the dosing controller 160 obtains the latest CGM, the latest velocity, and the latest ContinGlucosePrediction_wVelocity from the continuous glucose measurement using trend velocity program 600, as shown in FIG. 5. At operation 904, the dosing controller 160 determines if a sensor failure has occurred, and, if a sensor failure has occurred, a prompt is issued at operation 906 for an EGM. At operation 912, the dosing controller 160 determines whether the temporal relationship between the latest EGM check and the latest CGM are closer together than or equal to one timer interval Time_IntervalCGM. If the dosing controller 160 determines that the absolute value of the difference between the latest CGM check and the latest CGM check is less than or equal to the Time_IntervalCGM, then the dosing controller 160 calculates a CGM error (CGMerr) and a CGM error percentage (CGMerr %) at operation 914 using the following equations:

$$CGMerr = |CGM - EGM| \tag{4}$$

-continued
$$CGMerr \% = \frac{CGMerr}{EGM} \tag{5}$$

If, at operation 912, the dosing controller 160 determines that the absolute value of the time difference between the latest EGM check and the latest CGM check is greater than the Time_IntervalCGM, then the dosing controller 160, at operation 916, displays message "Time not close enough" on one or more of the patient device 110, the HCP device 140, and/or the service provider 130.

At operation 918, the dosing controller 160 determines whether the CGM error is greater than a CGM error limit (CGMerrLimit), which, in some implementations, may be +—15 mg/dL for blood glucose less than or equal to 75 mg/dL and none for blood glucose greater than 75 mg/dL. If no, the dosing controller 160, at operation 920, checks if the percent CGM error (CGMerror %) is greater than a configurable CGM percent error limit (CGMerror % Limit). If the dosing controller 160 determines that neither of the conditions is met at 918 nor 920, the dosing controller 160 returns to the point of request at operation 926. If the dosing controller determines that either of the conditions of operations 918 and 920 is satisfied at operation 922, then the dosing controller 160 proceeds to control by EGM at operation 924.

Figure 9:
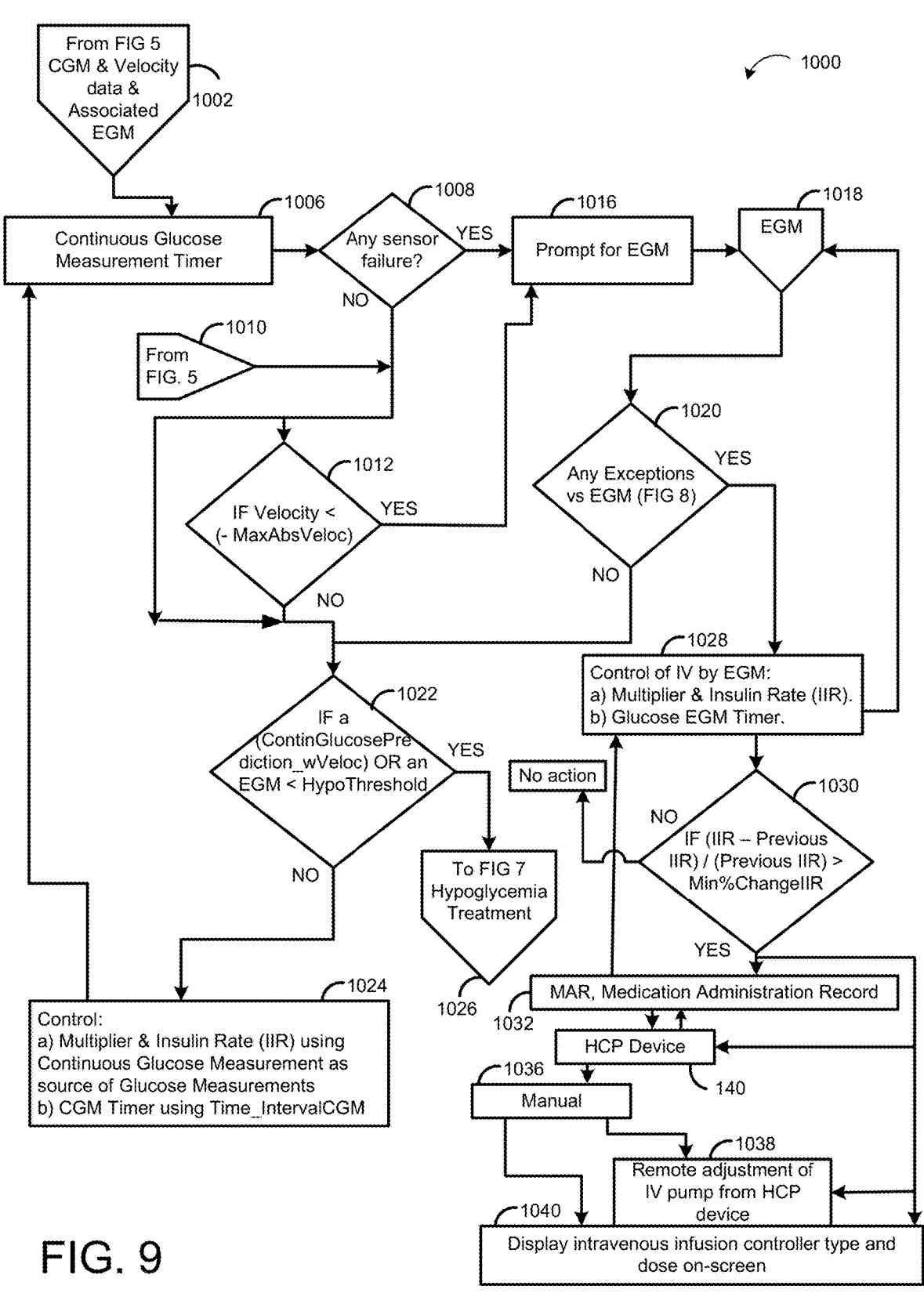
FIG. 9 is a schematic view of an exemplary intravenous (IV) insulin adjusted by continuous glucose measurement program of the system of FIGS. 1A-1C.

Referring to FIG. 9, an intravenous (IV) insulin adjusted by continuous glucose measurement program 1000 is generally shown, whereby the program 1000 is executed by the dosing controller 160 and starts at operations 1002 and 1004 where the dosing controller 160 obtains the latest CGM and velocity data and the associated EGM from FIG. 5. At operation 1006, the dosing controller 160 is in a loop controlled by the CGM timer, with time intervals based on the manufacturer's data, including statistical variability of the manufacturer's CGM data and the maximum CGM velocity permitted by the dosing controller 160. At operation 1008, the dosing controller 160 determines whether there is any sensor failure message. If so, a prompt is issued at 1016 for an EGM which enters the process at 1018. If there is no sensor failure, the dosing controller 160, at operation 1010, obtains a velocity and, at operation 1012, determines whether the velocity is less than a negative max absolute velocity (MaxAbsVeloc), which, in some implementations, may be equal to 3 mg/dL/min. If no, the dosing controller 160 proceeds to 1022. If the velocity is less than the negative of (MaxAbsVeloc) the dosing controller 160 prompts for an EGM at 1016.

If, at operation 1008, the dosing controller 160 determines that there is sensor failure, then the dosing controller 160 executes a prompt for a glucose measurement at operation 1016, and obtains an EGM at operation 1018. At operation 1020, the dosing controller 160 determines if there are any exceptions to the EGM (using the comparison exceptions program 900 shown in FIG. 8). If no, the dosing controller 160, at operation 1022, determines whether the ContinGlucosePrediction_wVelocity or the EGM is less than a predetermined hypoglycemia threshold, which, in some implementations, may be equal to 70 mg/dL. If no, then, at operation 1024, the dosing controller 160 determines that (a) a multiplier and insulin rate (IIR) using CGM as the source of glucose measurements and (b) the CGM timer control the IV insulin treatment. If, at operation 1022, the dosing controller 160, determines that the ContinGlucosePrediction_wVelocity or the EGM is less than the pre-determined hypoglycemia threshold, then the program 1000, at operation 1026, proceeds to the hypoglycemia treatment program 800, as shown in FIG. 7.

If, at operation 1020, the dosing controller 160 determines that there are exceptions to the EGM, then, at operation 1028, the dosing controller 160 determines that (a) the IIR using the EGM as the source of glucose measurements and (b) the EGM timer control the IV insulin treatment, and returns to the EGM at operation 1018. At operation 1030, the dosing controller 160 determines whether the difference between the current IIR and the previous IIR divided by the previous IIR is greater than the minimum percent change in IIR (Min % ChangeIIR), which, in some implementations, may be equal to 5%. The current IIR may be from either CGM control or EGM control. If the % change is above the minimum % change, then the dosing controller 160 transmits the newly-calculated insulin rate IIR to the MAR of the patient 10 at operation 1032, directly to the dose-administration device, such as an intravenous infusion controller 1040, and transmits the IIR to the HCP device 140, so the HCP can adjust the dose-administration device 1040 directly or remotely at operation 1038. In some implementations, the dose administration device, which in this case is an intravenous infusion controller may also be controlled directly and automatically from operation 1030. At operation 1036, the HCP 40 adjusts the IV pump of the patient 10 manually, or at operation 1038, the dosing controller 160 adjusts the IV pump of the patient 10 remotely. The dosing controller 160 reports all adjustments of the IIR to the MAR 1032.

Figure 10:
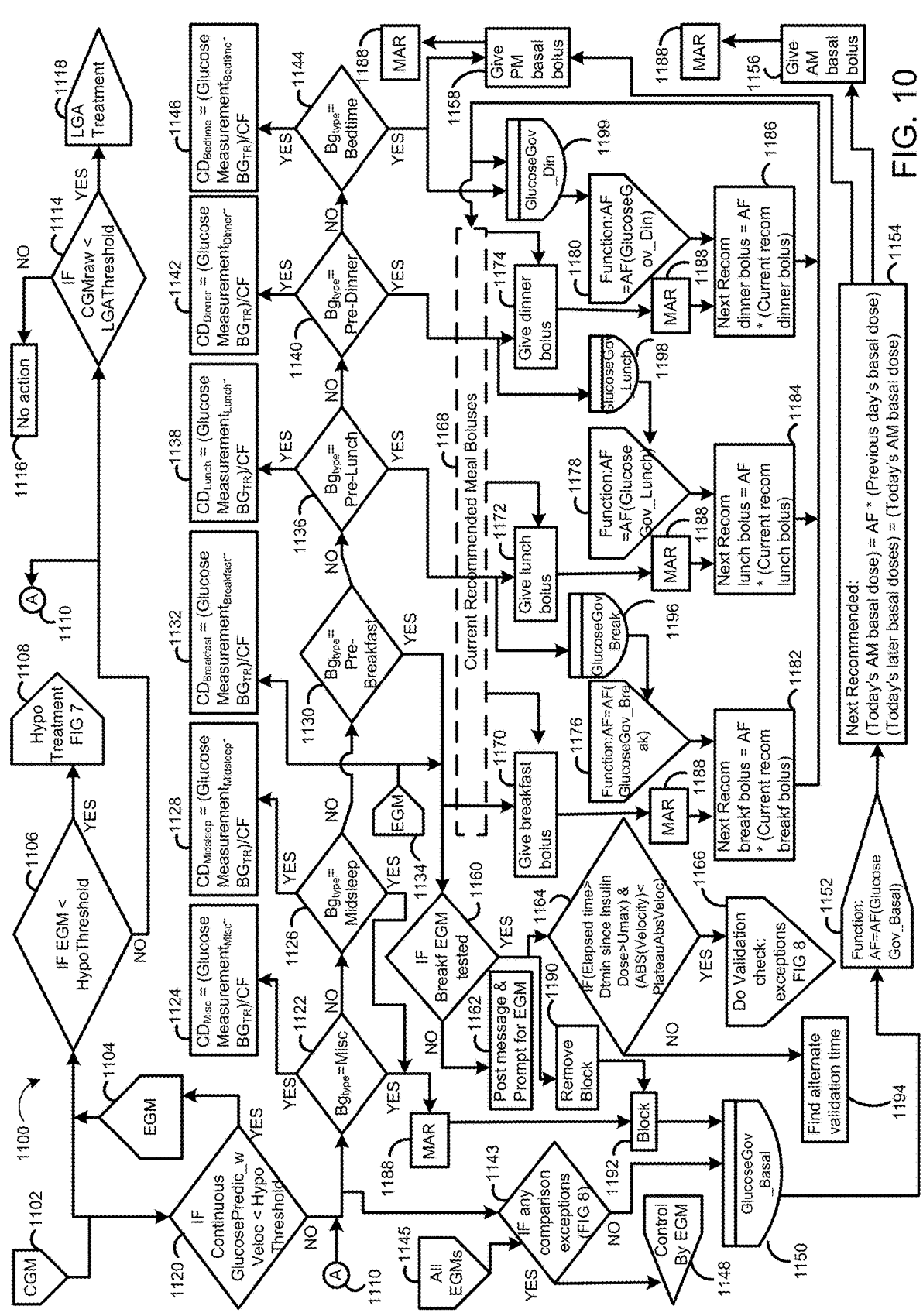
FIG. 10 is a schematic view of an exemplary subcutaneous insulin adjusted by continuous glucose measurement program of the system of FIGS. 1A-1C.

Referring to FIG. 10, subcutaneous insulin adjusted by continuous glucose measurement program 1100 is generally shown, whereby the program 1100 is executed by the dosing controller 160 and starts at operation 1102 where the dosing controller obtains data from the CGM through FIG. 5 which also provides velocity data as measured by the CGM device and calculates a Velocity-based prediction of the continuous glucose measurement at a configurable time in the future (ContinGlucosePredic_wVelocity). At operation 1120 the process determines if ContinGlucosePredic_wVelocity, is less than the hypoglycemia threshold. If YES, then a prompt is issued for an Episodic Glucose Measurement (EGM), which may be a finger-stick measurement of capillary blood, a laboratory-analyzed measurement, an arterial sample, or any other one-time measurement of glucose concentration. The term "Glucose Measurement" as used herein refers to an EGM or (ContinGlucosePredic wVelocity) in that preferential priority, because the velocity prediction reduces interstitial delay of the CGM measurement to a negligible amount, so that the (ContinGlucosePredic wVelocity) is for the same time as the real-time EGM. The raw CGM measurement is not used except as noted. At operation 1104, the dosing controller 160 obtains the current EGM for the patient 10.

All EGM's enter the process at operation 1145 and are sent by operation 1143 to the exceptions checker, of FIG. 8, and if exceptions are found by FIG. 8, operation 1143, instructs operation 1148 to shift SubQ control to EGM control. At operation 1106, the dosing controller 160 determines if the current EGM is less than the hypoglycemia threshold, and, if yes, the dosing controller 160 executes the hypoglycemia treatment program 800, as shown in FIG. 7, at operation 1108. If no, the dosing controller 160 proceeds to operation 1110 illustrated as an encircled A, and the dosing controller 160 continues to operation 1114. At 1114 the dosing controller 160 determines whether the raw CGM (without velocity based prediction) is less than an LGA threshold. If no, then the dosing controller 160 takes no action at operation 1116. If yes, the dosing controller 160 proceeds to an LGA (Low Glucose Alert) treatment at operation 1118.

At operation 1120, if the next CGM predicted for the current velocity is not less than the hypoglycemia threshold, then the dosing controller 160 proceeds to determine the time interval identified by the glucose type (BG$_{type}$). At operation 1122, the dosing controller 160 determines whether the BG type is miscellaneous. If yes, the dosing controller 160, at operation 1124, calculates the miscellaneous correction dose (CDmisc) as the difference between the available glucose measurement minus the target blood glucose (BG$_{TR}$) and this difference is divided by the correction factor (CF), where the target blood glucose and the correction factor are tailored to each specific patient 10. The dosing controller 160 issues a prompt for the correction dose to be given to the patient and when a response indicates completed, the given dose is recorded in the Medical Administration Record (MAR) 1188. A block is placed at operation 1192 from midnight until breakfast where the block is on the flow of information into operation 1150 whose purpose is to determine a governing glucose measurement for Basal. If, at operation 1122, the dosing controller 160 determines that the BG type is not miscellaneous, then the dosing controller 160, at operation 1126, determines whether the BG type is midsleep. If yes, the dosing controller 160 calculates the correction dose for midsleep at operation 1128. A prompt is issued for a correction dose, the given dose is entered by the nurse and recorded in the MAR.

If, at operation 1126, the dosing controller 160 determines that the BG type is not midsleep, then the dosing controller 160 proceeds to operation 1130 to determine whether the BG type is breakfast. If, at operation 1160, the dosing controller 160 determines that the breakfast EGM was not tested, then the dosing controller 160, at operation 1162, displays a message on one or more of the patient device 110, the HCP device 140, and/or the service provider 130 indicating that the pre-breakfast EGM was not tested and executes a prompt for an EGM. A block on the flow of information into the Basal adjustment sequence has existed at operation 1192 since midnight. If, at operation 1160, the dosing controller 160 determines that the breakfast EGM was tested, then the dosing controller 160 lifts the block on the flow of information to the basal adjustment sequence at operation 1190 and allows the breakfast EGM to pass the block also. If the breakfast EGM was tested then the dosing controller 160, at operation 1164, determines whether it has been (DTmin) or more hours since any insulin dose greater than (Umax) units, and the absolute value of the velocity is less than a configurable moderate velocity limit (PlateauAbsVeloc, suggested value 2.0 mg/dL/minute) indicating a near-zero velocity plateau suitable for a validation check. If no, then the program 1100 continues to look for an alternate time for a validation check at operation 1194. If yes, then the program 1100 proceeds to operation 1166 for a validation check as described in the comparison exceptions program 900 shown in FIG. 8.

If, at operation 1130, the dosing controller 160 determines that the BG type is pre-breakfast, then the dosing controller 160 at operation 1132, calculates the breakfast correction dose (CDbreakfast) as the difference between the available glucose measurement minus the target blood glucose (BG$_{TR}$) and this difference is divided by the correction factor (CF), where the target blood glucose and the correction factor are tailored to each specific patient 10. The dosing controller 160 issues a prompt for the correction dose to be given to the patient and when a response indicates completed, the given dose is recorded in the Medical Administration Record (MAR) 1188. In some Embodiments the breakfast correction dose and the breakfast meal bolus may be given as a combined bolus. Then the dosing controller obtains the current recommended breakfast meal bolus at 1168 and issues a prompt for the administration of the breakfast meal bolus to the patient 10 at operation 1170, e.g., using the administration device 123. The given doses are recorded in the MAR 1188. The feed of glucose measurements into 1150 was blocked at midnight by 1192 and has awaited the breakfast glucose to be unlocked. Now at breakfast with the EGM tested, the block on the flow of information into the basal adjustment sequence has been lifted by operation 1190 and the breakfast EGM has also been tested. The dosing controller 160 determines from the MAR at operation 1188 if the breakfast glucose was followed by treatment. The condition of "treated" signifies treatment by insulin, oral carbohydrates, intravenous glucose (D-50), Glucagon, or Correction Dose of Insulin. At block 1150 the dosing controller 160 determines a governing glucose for Basal as (GlucoseGov_Basal)=MIN[Treated Glucose Measurement in interval [{Time of previous night's Basal+NightStartMargin} to Breakfast], where each candidate glucose measurement is not within a time separation DTmin of any insulin dose>Umax. The calculations of GlucoseGov_Basal at 1150 may be calculated at a time after the breakfast glucose measurement becomes available. The constants NightStartMargin, DTmin and Umax are configurable. At operation 1152, the dosing controller 160 determines the adjustment factor (AF), which is a function of the governing glucose value for basal (GlucoseGov_Basal), which may be accomplished by referring to an Adjustment Factor Table or other suitable method. At operation 1154, the dosing controller 160 determines (i) today's recommend AM basal dose as equal to the adjustment factor multiplied by the previous day's last basal dose, and (ii) today's later recommended basal doses as equal to today's AM basal dose. At operation 1156, the dosing controller 160 issues a prompt for the administration of the AM basal dose to the patient 10, e.g., using the administration device 123, and when the time is appropriate at bedtime at operation 1158, the dosing controller 160 issues a prompt for the administration of the PM basal dose to the patient 10, e.g., using the administration device 123, and when the basal dose is given, it is recorded in the MAR 1188.

If, at operation 1130, the dosing controller 160 determines that the BG type is not pre-breakfast, then the dosing controller 160 determines whether the BG type is pre-lunch at operation 1136. If the BG type is pre-lunch the dosing controller 160 calculates the correction dose at operation 1138 by taking the difference between the glucose measurement at lunch and the blood glucose target divided by the correction factor. The dosing controller 160 obtains the current recommended lunch bolus from 1168 and prompts for administration of this lunch bolus to the patient 10 at operation 1172, e.g., using the administration device 123. In some embodiments the correction dose and meal bolus are combined. The given doses pertaining to the lunch bolus are recorded in the MAR 1188. The determination of a governing glucose measurement for the adjustment of the next day's breakfast bolus is shown at operation 1196 by the following formula: GlucoseGov_Break=First-occurring of [(Glucose_Measurement_Lunch) or any treated Glucose Measurement less than the Low Glucose Alert (LGA) threshold occurring since Breakfast bolus]. Treated means treatment by oral carbohydrates, intravenous glucose, glucagon, or Correction Dose of Insulin. A suggested source of the status of treatment is the MAR. At operation 1176, the dosing controller 160 determines the adjustment factor for the breakfast bolus as a function of the governing blood glucose (GlucoseGov Break) and the target range, where the function may be accomplished by a table or other suitable method, and then uses this adjustment factor at operation 1182 to determine the next recommended breakfast bolus. The dosing controller 160 stores the next recommended breakfast bolus at block 1168 for use the next day.

If, at operation 1136, the dosing controller 160 determines that the BG type is not pre-lunch, then the dosing controller 160 determines, at operation 1140, whether the BG type is pre-dinner. If yes, the dosing controller 160 obtains the tested pre-dinner glucose measurement and calculates the correction dose at operation 1142 by taking the difference between the glucose measurement at dinner and the blood glucose target divided by the correction factor. In some embodiments the correction dose and the Dinner Meal Bolus are given together as a combined dose. The dosing controller 160 obtains the current recommended dinner bolus from 1168 prompts for is administration to the patient 10 at operation 1174, e.g., using the administration device 123. The dosing controller 160 then records the given doses in the MAR. The governing glucose measurement for the adjustment of the next day's Lunch bolus is shown by the following formula at block 1198: (GlucoseGov_Lunch) =The first occurring of [(Glucose measurement before dinner) or any treated glucose measurement less than (LGAthreshold) since the Lunch bolus]. Treated means treatment by: Oral carbohydrates, Intravenous glucose, Glucagon, or Correction Dose of insulin. A suggested source of information about treatments given is the MAR. At operation 1178, the dosing controller 160 determines the adjustment factor for the next day's Lunch Bolus as a function of the governing blood glucose (GlucoseGov_Lunch) by consulting the Adjustment Factor Table, and then uses this adjustment factor in the calculation for the next day's Lunch bolus at operation 1184. The dosing controller 160 stores the next recommended Lunch bolus for next day's use at block 1168.

If, at operation 1140, the dosing controller 160 determines that the BG type is not pre-dinner, then the dosing controller 160 determines, at operation 1144, whether the BG type is bedtime. If yes, the dosing controller 160 obtains a glucose test, and calculates a correction dose at operation 1146 by calculating the difference between the glucose measurement at bedtime and the glucose target and dividing by the correction factor (CF). The correction dose is stored in the MAR 1188. The dosing controller 160 issues a prompt at 1158 for administration of a PM basal dose. The determination of the governing glucose measurement for the adjustment of the next day's dinner meal bolus is shown at operation 1199 by the following formula: GlucoseGov_Din=First-occurring of [(Glucose_Measurement_bedtime) OR any treated Glucose Measurement less than (LGAthreshold) since Dinner bolus]. Treated means treatment by oral carbohydrates, intravenous glucose, glucagon, or Correction Dose of insulin. A suggested source of information about treatments given is the MAR 1188.

At operation 1180, the dosing controller 160 determines the adjustment factor for the next day's dinner bolus as a function of the governing glucose measurement from block 1199 (GlucoseGov Din) using the adjustment factor table. At operation 1186, the next day's dinner bolus is calculated as the adjustment factor for dinner multiplied by the current recommended dinner bolus. This result is stored at 1168 for use the next day.

Figure 11:
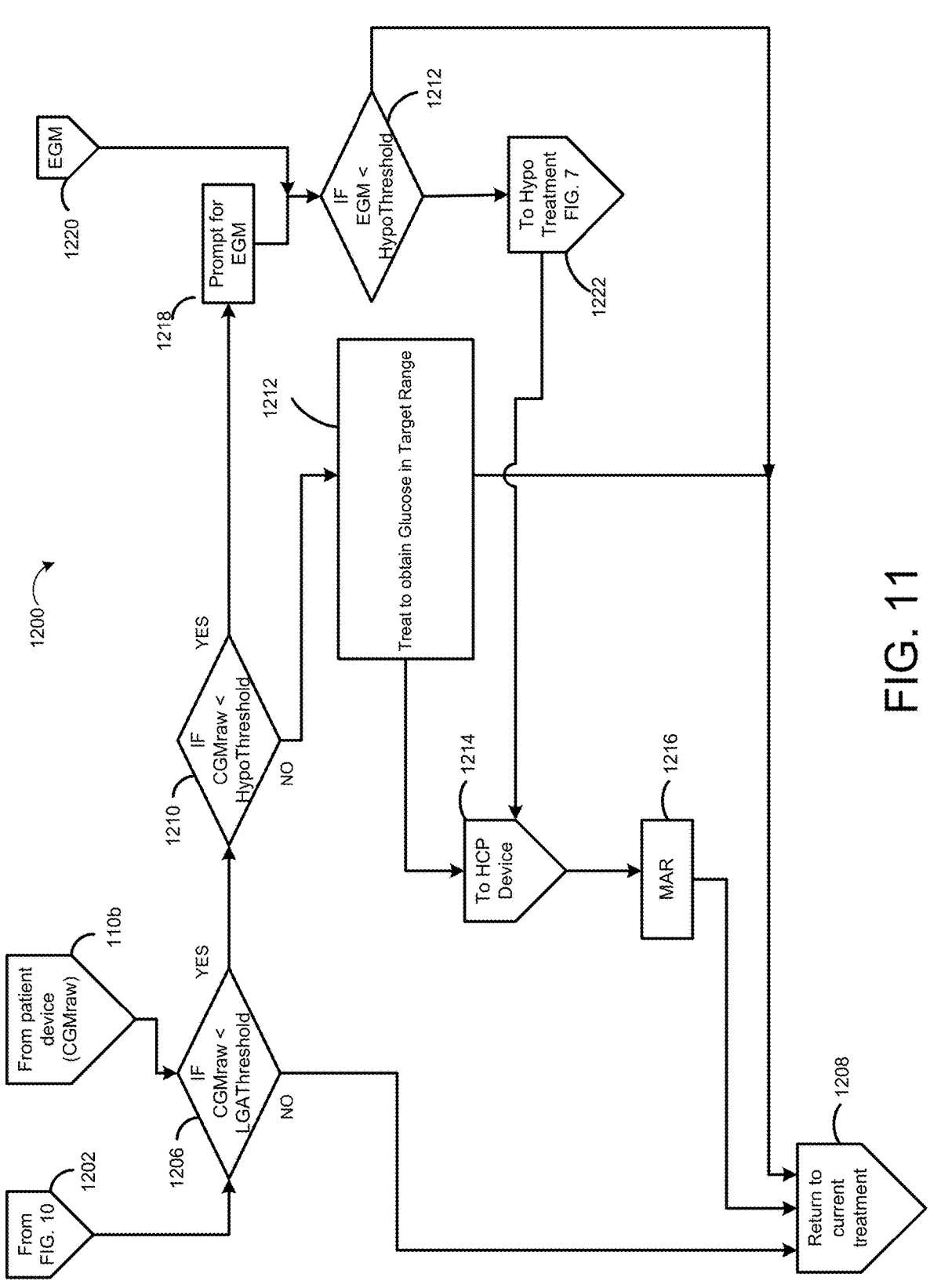
FIG. 11 is a schematic view of an exemplary low glucose alert (LGA) treatment program of the system of FIGS. 1A-1C.

Referring to FIG. 11, a Low Glucose Alert (LGA) program 1200 is generally shown, whereby the program 1200 is executed by the dosing controller 160, and includes a raw CGM value (mg/dL), without any velocity-based prediction, being sent whenever the raw CGM goes below an LGA threshold (LGAthreshold). This allows small doses of carbohydrate (LGAtreatCarb) to be given as preventive action to prevent hypoglycemia. The LGA program 1200 starts at operation 1202 by a prompt from the SubQ process of FIG. 10. The raw CGM measurement (CGMraw) enters the LGA process at operation 1204. The dosing controller 160, at operation 1206, compares the raw CGM to a configurable LGA threshold (LGAthreshold) (mg/dL). If the dosing controller 160 determines that the raw CGM is greater than or equal to the LGA threshold, then the dosing controller 160 returns to the current treatment at operation 1208. If the dosing controller 160 determines that the raw CGM is below the LGA Threshold, then the dosing controller 160, at operation 1210, compares the raw CGM to a configurable Hypoglycemia Threshold. If the dosing controller 160 determines that the raw CGM is greater than or equal to a configurable hypoglycemia threshold, then the dosing controller 160 transmits instructions at operation 1212 to treat to obtain Glucose Measurement in the target range.

The dosing controller 160 transmits the treatment instructions to the HCP device 140 at operation 1214. When the HCP administers the dose(s), his/her response is obtained by keying or digitally entering from one or more of the HCP device 140, a desktop or laptop computer, or any access device for the dosing controller 160. The dosing controller 160 transmits the response to the MAR 1188 at operation 1216, and the dosing controller 160 returns to the current treatment at operation 1208. If, at operation 1210, the dosing controller 160 determines that the raw CGM is less than the hypoglycemia threshold, the dosing controller 160 issues a prompt at operation 1218 for an EGM. The dosing controller 160 obtains the EGM at operation 1220 and determines at 1212 if the EGM is less than the hypoglycemia threshold. If so, the dosing controller 160 transmits the EGM to FIG. 7 Hypoglycemia Treatment at operation 1222. If, at operation 1212, the dosing controller 160 determines that the EGM is greater than or equal to the hypoglycemia threshold, then the dosing controller 160 returns the logic and information to the current treatment at operation 1208.

Figure 12:
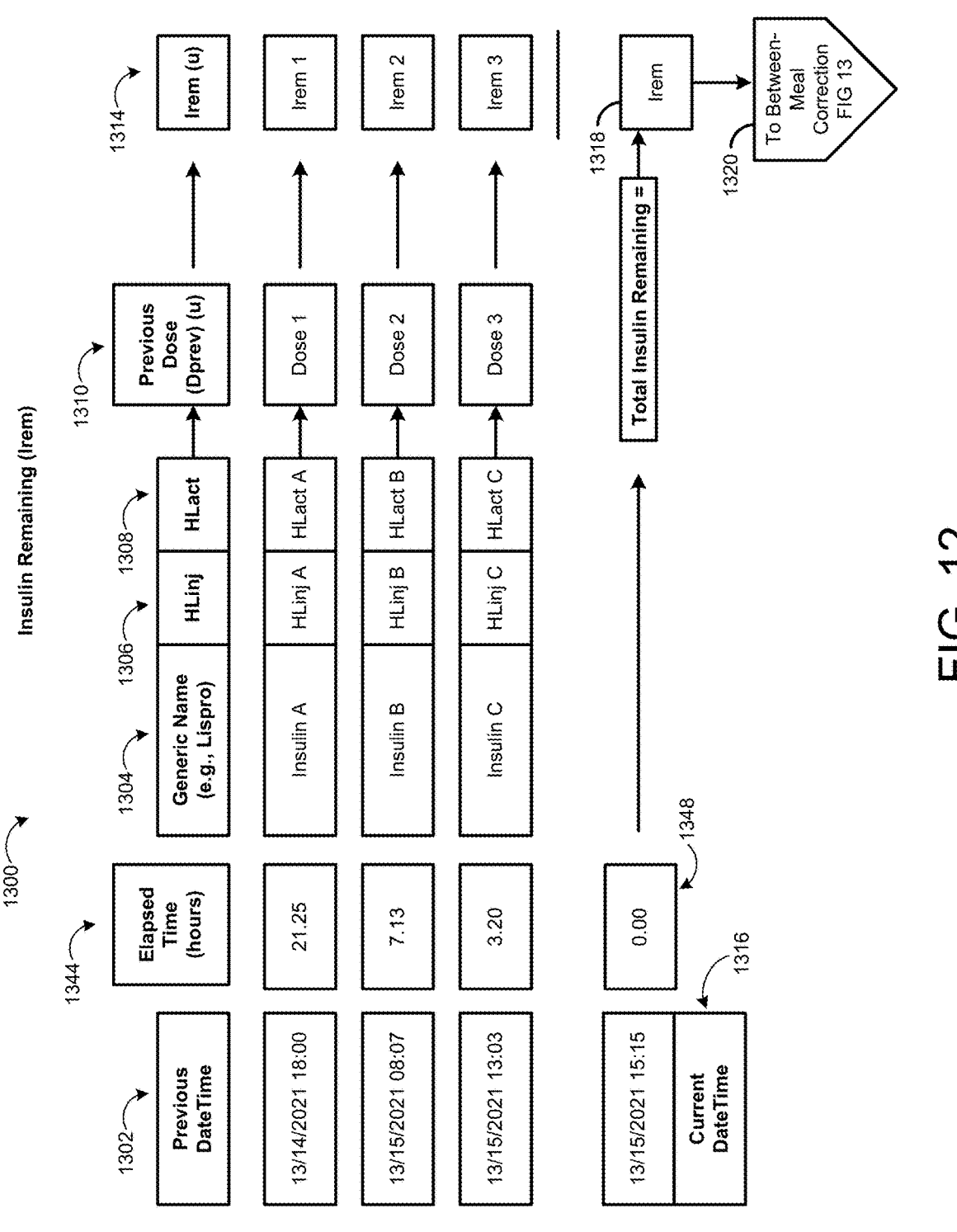
FIG. 12 is a schematic view of exemplary insulin remaining (Irem) program of the system of FIGS. 1A-1C.

Referring to FIG. 12, an insulin remaining (Irem) program 1300 is generally shown, whereby the program 1300 is executed by the dosing controller 160. The program 1300 includes a previous date-time 1302, a generic name for the insulin 1304, a half-life of insulin in the injection site (HLinj) 1306, a half-life of insulin active in the body (HLact) 1308, a previous dose (Dprev) 1310 in units, and an insulin remaining (Irem) 1314 in units. The data shown in FIG. 12 is exemplary and provided for illustration purposes only. The dosing controller 160 calculates the Irem using the following Equation 6:

$$Irem\text{(single dose)} = Dprev * \mathrm{EXP}\left(-(Tcurrent - Tdose) * \frac{0.693}{HLinj}\right) + $$

$$Dprev * \frac{\frac{0.693}{HLinj}}{\frac{0.693}{Hlact} - \frac{0.693}{HLinj}} * \left[\begin{array}{l} \mathrm{EXP}\left(-(Tcurrent - Tdose) * \frac{0.693}{HLinj}\right) - \\ \mathrm{EXP}\left(-(Tcurrent - Tdose) * \frac{0.693}{HLact}\right) \end{array}\right]$$

Figure 13:
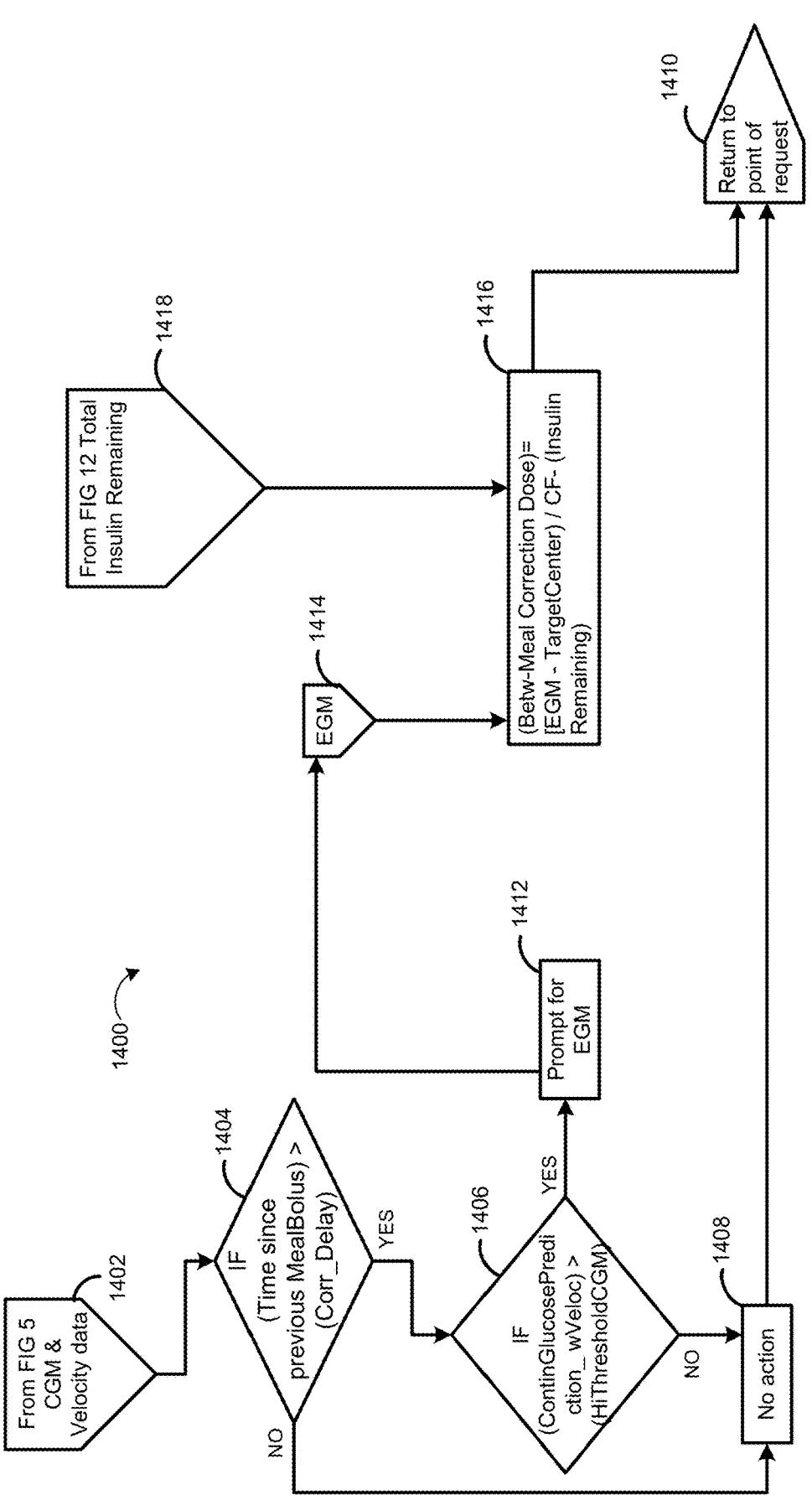
FIG. 13 is a schematic view of an exemplary between-meal correction dose with insulin-on-board program of the system of FIGS. 1A-1C.

As shown in FIG. 12, using the current date-time 1316, the dosing controller 160 calculates the total insulin remaining at 1318 and proceeds to operation 1320 to a between-meal correction program 1400 as shown in FIG. 13.

Referring to FIG. 13, the between-meal correction program 1400 is generally shown, whereby the program 1400 is executed by the dosing controller 160, and starts at operation 1402 where the dosing controller 160 obtains the glucose measurement. At operation 1404, the dosing controller 160 determines if the time since the previous meal bolus is greater than the correction delay. If yes, the dosing controller 160 proceeds to operation 1406, whereby the dosing controller 160 determines whether the continuous glucose prediction with veloc is greater than a configurable high threshold CGM (HiThresholdCGM). If no, then no action is taken at operation 1408 and the program 1400 returns to the point of request at operation 1410. Similarly, if at operation 1404, the dosing controller 160 determines that the time since the previous meal bolus is less than the correction delay, then no action is taken at operation 1408 and the program 1400 returns to the point of request at operation 1410. If, at operation 1406, the dosing controller 160 determines that the continuous glucose prediction with velocity is greater than a high threshold CGM, then the dosing controller 160 issues a prompt for an EGM at operation 1412 and obtains the EGM at operation 1414. Then the dosing controller 160, at operation 1416, determines a correction dose as equal to the difference between the glucose measurement and the target center divided by a configurable correction factor (CF) minus the insulin remaining, with the dosing controller 160 obtaining the Irem at operation 1418 from the Irem program 1300 in FIG. 12. Subsequently, the dosing controller 160 returns to the point of request at operation 1410.

Referring to FIG. 14, an exemplary arrangement of operations for a method 1500 of managing glucose levels of a patient 10 under the supervision of a HCP 40 includes, at operation 1502, obtaining, at data processing hardware 112, 142, 142, patient information for the patient 10 that includes patient medication data 404, patient monitoring data 416, and patient characteristic data 402, 408, 410, 412. The type of diabetes associated with the patient may include Type 1 Diabetes Mellitus, Type 2 Diabetes Mellitus, Gestational Diabetes Mellitus, Non-diabetic Stress Hyperglycemia, Maturity Onset Diabetes of the Young (MODY), Latent Autoimmune Diabetes in Adults (LADA), and unknown. The type of diabetes may also include any individual at risk of developing any of the aforementioned types of diabetes listed. The patient medication data may include a list of current medications including a list of medications and corresponding dosages the patient is currently prescribed. The patient characteristic data 402, 408, 410, 412 may include at least one of nutrition orders 402, MAR 408, EMR 410, and LIS 412.

At operation 1504, the method 1500 includes creating, by the data processing hardware 112, 142, 142, a patient risk profile based on the obtained patient information. The patient risk profile may be created based on an algorithm, or the obtained patient information may be compared to past, similar patient information to create match the current patient risk profile to a known patient risk profile created in the past.

At operation 1506, the method 1500 includes determining, by the data processing hardware 112, 132, 142, the likelihood that the patient 10 will experience hyperglycemic effects based on the patient risk profile. For example, if the patient risk profile includes medication data that is known to cause hyperglycemia, then the likelihood that the patient 10 will experience hyperglycemic effects is high. As another example, if the patient risk profile indicates that the patient follows a low-carbohydrate diet and a high exercise lifestyle, then the likelihood that the patient 10 will experience hyperglycemic effects is high.

At operation 1508, the method 1500 includes determining, by the data processing hardware 112, 132, 142, an optimum treatment plan for the patient 10 based on the patient risk profile and likelihood of experiencing hyperglycemic effects. For example, the optimum treatment plan for the patient 10 may be selected based on the therapy selection program 500 shown in FIG. 4. At operation 1510, the method 1500 includes transmitting, by the data processing hardware 112, 132, 142, the optimum treatment plan for the patient 10 to the HCP device 140 or the patient device 110. At operation 1512, the method 1500 includes executing, by the data processing hardware 112, 132, 142, the optimum treatment plan by an administration device associated with the patient 10. The administration device may include: the insulin pump 123, 123a; the smart pen 123, 123b; the smart pill bottle 123c; the smart pill 123d; or the insulin inhaler 123e.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

Implementations of the subject matter and the functional operations described in this specification can be implemented in digital electronic circuitry, or in computer software, firmware, or hardware, including the structures disclosed in this specification and their structural equivalents, or in combinations of one or more of them. Moreover, subject matter described in this specification can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter affecting a machine-readable propagated signal, or a combination of one or more of them. The terms "data processing apparatus", "computing device" and "computing processor" encompass all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as an application, program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

One or more aspects of the disclosure can be implemented in a computing system that includes a backend component, e.g., as a data server, or that includes a middleware component, e.g., an application server, or that includes a frontend component, e.g., a client computer having a graphical user interface or a Web browser through which a user can interact with an implementation of the subject matter described in this specification, or any combination of one or more such backend, middleware, or frontend components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specifics, these should not be construed as limitations on the scope of the disclosure or of what may be claimed, but rather as descriptions of features specific to particular implementations of the disclosure. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multi-tasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

A number of implementations have been described. Nevertheless, it will be understood that various modifications may be made without departing from the spirit and scope of the disclosure. Accordingly, other implementations are within the scope of the following claims. For example, the actions recited in the claims can be performed in a different order and still achieve desirable results.

What is claimed is:

1. A computer-implemented method executed on data processing hardware that causes the data processing hardware to perform operations comprising:

obtaining patient medication data comprising a current medications list including a list of medications a patient is currently prescribed, wherein at least one medication in the list of medications is not a medication for treating diabetes;

for each corresponding medication in the current medications list, determining corresponding risk profile characteristic data indicating a list of patient characteristics associated with hyperglycemia for patients receiving the corresponding medication and an amount of risk that the corresponding medication may cause increased hyperglycemia, wherein the amount of risk is determined based on a tiered glycemic formulary database organized in ranked tiers based upon a severity and likelihood that the corresponding medication will induce a hyperglycemic effect on the patient;

determining a likelihood that the patient will experience hyperglycemic effects based on the corresponding risk profile characteristic data determined for each corresponding medication in the list of medications the patient is currently prescribed;

determining an optimum treatment plan for the patient based on the likelihood that the patient will experience hyperglycemic effects, the optimum treatment plan comprising a recommended dosage of a particular medication, the particular medication comprising an anti-diabetes medication or insulin; and transmitting instructions to an administration device associated with the patient to administer the recommended dosage of the particular medication to the patient, the instructions causing the administration device to administer the recommended dosage of the particular medication to the patient.

2. The method of claim 1, wherein the operations further comprise transmitting the optimum treatment plan to at least one of a patient device associated with the patient or a healthcare professional (HCP) device associated with a HCP supervising treatment of the patient.

3. The method of claim 1, wherein the patient is diagnosed with one of Type 1 diabetes mellitus, Type 2 diabetes mellitus, gestational diabetes mellitus, non-diabetic stress hyperglycemia, Maturity Onset Diabetes of the Young (MODY), Latent Autoimmune Diabetes in Adults (LADA), or unknown.

4. The method of claim 1, wherein the patient medication data further comprises corresponding dosages for the list of medications the patient is currently prescribed.

5. The method of claim 1, wherein the patient medication data comprises a drug name, a dosage, a route of administration, a frequency, and a time of administration of any medications in the current medications list known to impact patient glucose levels that the patient is currently prescribed.

6. The method of claim 1, wherein the operations further comprise:

obtaining patient monitoring data for the patient, the patient monitoring data comprising at least one of:

one or more glucose values for the patient; or an A1c value for the patient, wherein determining the likelihood that the patient will experience hyperglycemic effects is further based on the patient monitoring data for the patient.

7. The method of claim 1, wherein the operations further comprise:

obtaining patient characteristic data for the patient, wherein determining the likelihood that the patient will experience hyperglycemic effects is further based on the patient characteristic data for the patient.

8. The method of claim 7, wherein the patient characteristic data comprises at least one of:

nutrition order data associated with the patient;

a medical administration record (MAR) associated with the patient;

an electronic medical record (EMR) associated with the patient; or laboratory information system (LIS) data associated with the patient.

9. The method of claim 7, wherein the operations further comprise:

creating a patient risk profile for the patient based on the patient medication data and the patient characteristic data, wherein determining the optimum treatment plan for the patient based on the likelihood that the patient will experience hyperglycemic effects is further based on the patient risk profile.

10. The method of claim 9, wherein creating the patient risk profile is further based on medical literature.

11. A system comprising:

data processing hardware; and memory hardware in communication with the data processing hardware and storing instructions that, when executed by the data processing hardware, causes the data processing hardware to perform operations comprising:

obtaining patient medication data comprising a current medications list including a list of medications a patient is currently prescribed, wherein at least one medication in the list of medications is not a medication for treating diabetes;

for each corresponding medication in the current medications list, determining corresponding risk profile characteristic data indicating a list of patient characteristics associated with hyperglycemia for patients receiving the corresponding medication and an amount of risk that the corresponding medication may cause increased hyperglycemia, wherein the amount of risk is determined based on a tiered glycemic formulary database organized in ranked tiers based upon a severity and likelihood that the corresponding medication will induce a hyperglycemic effect on the patient;

determining a likelihood that the patient will experience hyperglycemic effects based on the corresponding risk profile characteristic data determined for each corresponding medication in the list of medications the patient is currently prescribed;

determining an optimum treatment plan for the patient based on the likelihood that the patient will experience hyperglycemic effects, the optimum treatment plan comprising a recommended dosage of a particular medication, the particular medication comprising an anti-diabetes medication or insulin; and transmitting instructions to an administration device associated with the patient to administer the recommended dosage of the particular medication to the patient, the instructions causing the administration device to administer the recommended dosage of the particular medication to the patient.

12. The system of claim 11, wherein the operations further comprise transmitting the optimum treatment plan to at least one of a patient device associated with the patient or a healthcare professional (HCP) device associated with a HCP supervising treatment of the patient.

13. The system of claim 11, wherein the patient is diagnosed with one of Type 1 diabetes mellitus, Type 2 diabetes mellitus, gestational diabetes mellitus, non-diabetic stress hyperglycemia, Maturity Onset Diabetes of the Young (MODY), Latent Autoimmune Diabetes in Adults (LADA), or unknown.

14. The system of claim 11, wherein the patient medication data further comprises corresponding dosages for the list of medications the patient is currently prescribed.

15. The system of claim 11, wherein the patient medication data comprises a drug name, a dosage, a route of administration, a frequency, and a time of administration of any medications in the current medications list known to impact patient glucose levels that the patient is currently prescribed.

16. The system of claim 11, wherein the operations further comprise:

obtaining patient monitoring data for the patient, the patient monitoring data comprising at least one of:

one or more glucose values for the patient; or an A1c value for the patient, wherein determining the likelihood that the patient will experience hyperglycemic effects is further based on the patient monitoring data for the patient.

17. The system of claim 11, wherein the operations further comprise:

obtaining patient characteristic data for the patient, wherein determining the likelihood that the patient will experience hyperglycemic effects is further based on the patient characteristic data for the patient.

18. The system of claim 17, wherein the patient characteristic data comprises at least one of:

nutrition order data associated with the patient;

a medical administration record (MAR) associated with the patient;

an electronic medical record (EMR) associated with the patient; or laboratory information system (LIS) data associated with the patient.

19. The system of claim 17, wherein the operations further comprise:

creating a patient risk profile for the patient based on the patient medication data and the patient characteristic data, wherein determining the optimum treatment plan for the patient based on the likelihood that the patient will experience hyperglycemic effects is further based on the patient risk profile.

20. The system of claim 19, wherein creating the patient risk profile is further based on medical literature.

* * * * *